United States Patent [19]
Hibbs et al.

[11] Patent Number: 5,859,314
[45] Date of Patent: Jan. 12, 1999

[54] MICE WITH TARGETED TYROSINE KINASE, LYN, DISRUPTION

[75] Inventors: Margaret L. Hibbs; Ashley R. Dunn; Dianne Graill; George Hodgson; David M. Tarlington, all of Parkville; Jane Armes, Heidelberg, all of Australia

[73] Assignee: Ludwig Institute for Cancer Research, New York, N.Y.

[21] Appl. No.: 730,876

[22] Filed: Oct. 18, 1996

[51] Int. Cl.$^6$ ..................... C12N 15/00
[52] U.S. Cl. ............ 800/2; 435/172.3; 800/DIG. 1; 800/DIG. 3; 800/DIG. 4; 424/9.1; 424/9.2
[58] Field of Search ............ 800/2, DIG. 1–4; 435/172.3, 6; 424/9.1, 9.2; 514/44, 2

[56] References Cited

U.S. PATENT DOCUMENTS

| | | | |
|---|---|---|---|
| 5,221,778 | 6/1993 | Byrne et al. | 800/2 |
| 5,545,808 | 8/1996 | Hew et al. | 800/2 |

OTHER PUBLICATIONS

Salter, et al. Transgenic Chickens: Insertion of Retroviral Genes into the Chicken Germ Line. Virology, vol. 157, pp. 236–240, 1987.

Houdebine, L. M. Production of pharmaceutical proteins from transgenic animals. J. of Biotech. vol. 34, pp. 269–287, 1994.

NIH panel. Report and recommendations of the panel to assess the NIH investment in research on gene therapy, Dec. 7, 1995.

Bradley et al. Modifying the mouse: design and desire. Biotechnology, vol. 10, pp. 534–539, May 1992.

Fassler et al. Knockout Mice: How to make them and why. The immunological approach. Int. Arch. Allergy Immunol., vol. 106, pp. 323–334, 1995.

*Primary Examiner*—Jasemine C. Chambers
*Assistant Examiner*—Deborah J. R. Clark
*Attorney, Agent, or Firm*—Felfe & Lynch

[57] ABSTRACT

A non-human animal carrying a disruption of a gene encoding a lyn protein tyrosine kinase provides a convenient system for the study of diseases associated with or caused by lyn deficiency, and for the testing of therapeutic agents for the treatment or prevention of diseases which include autoimmune diseases, allergy, asthma and malignant disease.

22 Claims, 13 Drawing Sheets

Days Post Immunization

FIG. 5A(ii)

Days Post Immunization

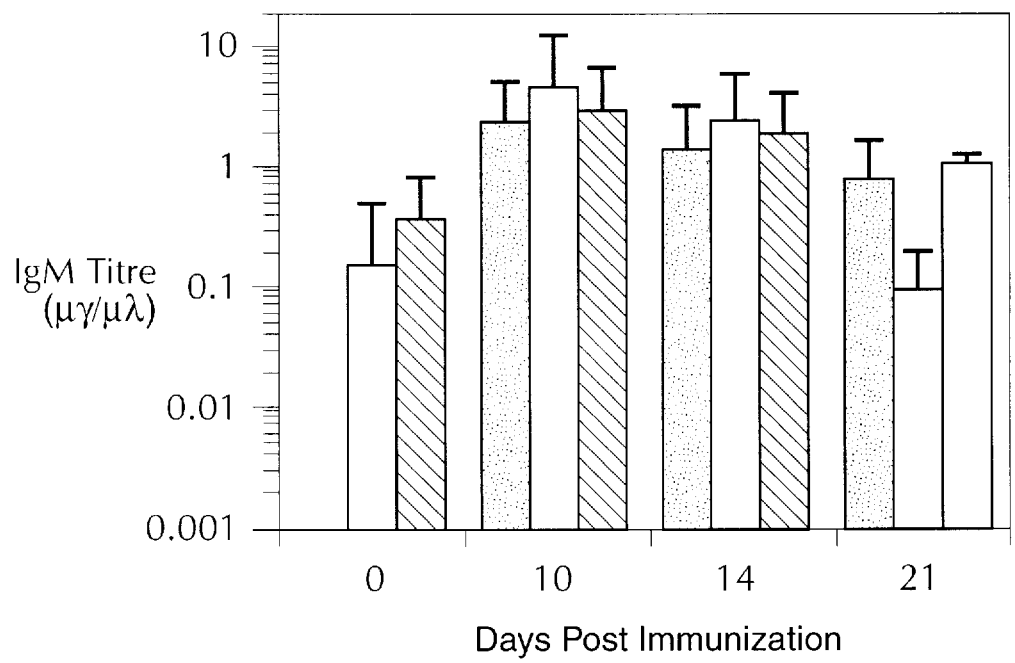
FIG. 5B(i)
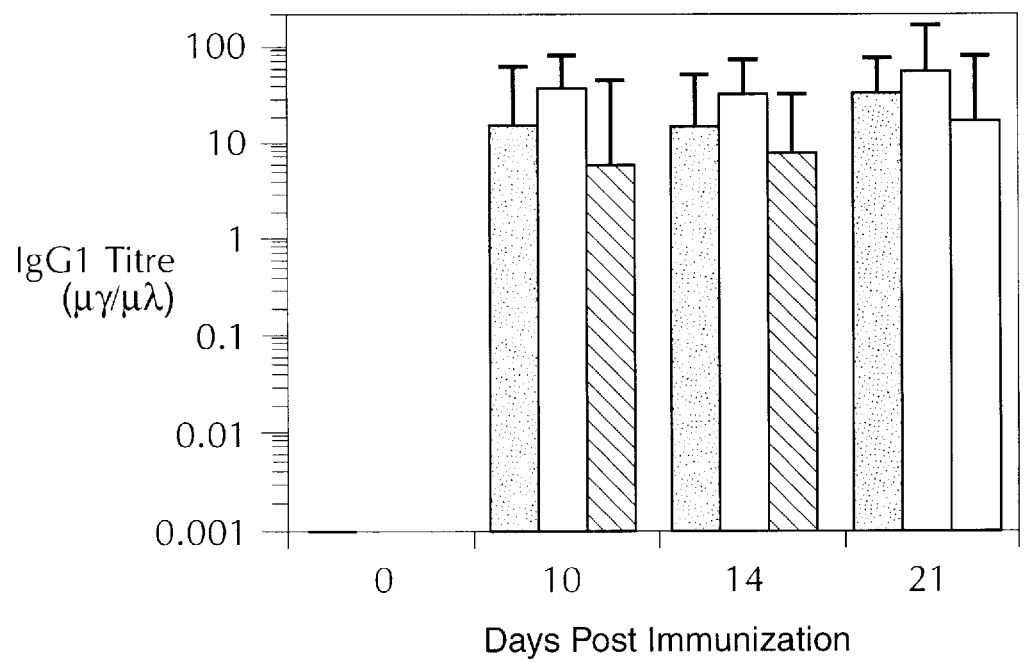
FIG. 5B(ii)

FIG. 6A
FIG. 6B
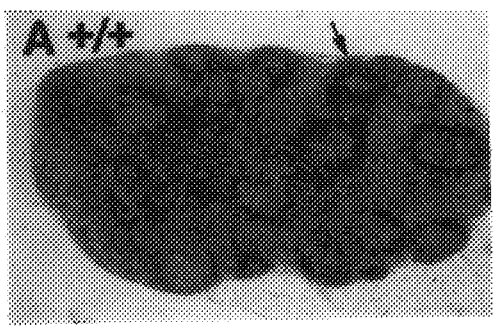
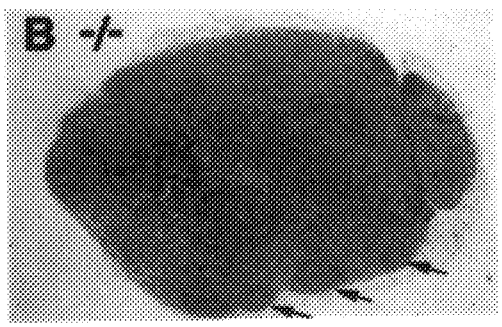
FIG. 6C
FIG. 6D
FIG. 6E
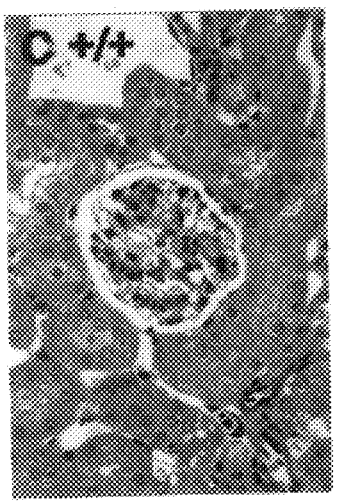
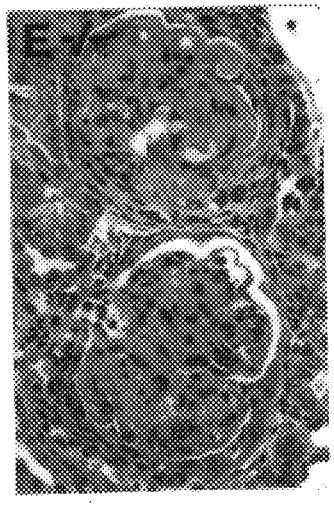
FIG. 6F
FIG. 6G
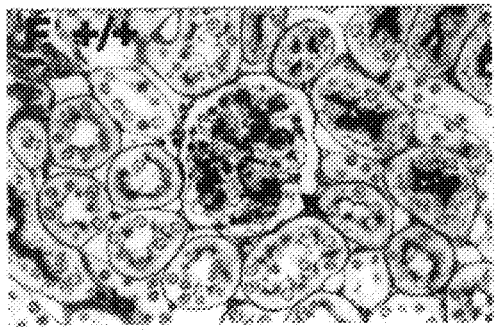
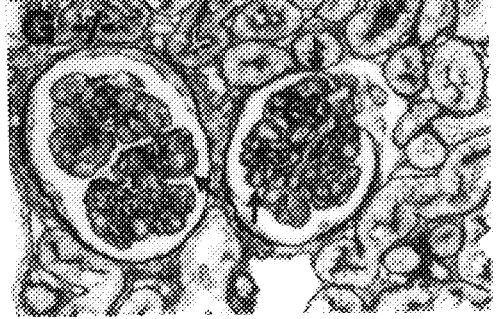

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

ATGGGGAATG GTGGAAAGCT      20

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

ACTTCCCCAA ACTGCCCTGC      20

( 2 ) INFORMATION FOR SEQ ID NO: 3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CTGGGGGGTC GGTCTAGCTG C      21

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GGTATCCTCA GAGCCCTCCA C      21

( 2 ) INFORMATION FOR SEQ ID NO: 5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TGCTACTTCC ATTTGTCACG TCC      23

( 2 ) INFORMATION FOR SEQ ID NO: 6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (xi) SEQUENCE DESCRIPTION: SEQ ID NO: 6:

ACAGAGCTAG ACCGTTCTTT CCTC                                              24

(2) INFORMATION FOR SEQ ID NO: 7:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO: 7:

CAGGTGGAGC ATACCTGGCT GTTT                                              24

MICE WITH TARGETED TYROSINE KINASE, LYN, DISRUPTION

This invention relates to model systems for autoimmune disease. In particular, the invention relates to animals, preferably mice, with a specifically-targeted disruption of a gene encoding a protein tyrosine kinase enzyme of the src family. Mice according to the invention show a variety of perturbations of the immune system, and at the age of six weeks more than 90% develop early signs of autoimmune glomerulonephritis.

BACKGROUND OF THE INVENTION

For many tissues of the body, ordered growth requires that the balance between cell production, cell differentiation and cell death is precisely regulated. Among the best studied of the rapidly-turning over tissues is the haematopoietic system, in which a multitude of terminally-differentiated cell types is generated from a relatively small number of stem cells and committed progenitor cells. Many of the factors which participate in the regulation of this process are known, thanks to data largely generated using in vitro systems. Recently, it has been possible to use gene targeting in embryonic stem cells (ES cells) to generate mice deficient in growth regulators, in order to examine whether these growth regulators indeed play a pivotal role in the regulation of normal blood cell production. See International Patent Application No. WO 95/23862 (PCT/AU94/00103).

Cells of the immune system are subject not only to regulation by a variety of growth factors and cytokines, but also utilise a complex system of signal transduction to mediate cell activation following antigen stimulation.

In particular, the src family of protein tyrosine kinases has been implicated in cell signalling through the physical association of these kinases with different cell surface receptors which on their own lack intrinsic catalytic activity (Bolen et al, 1992). Like several other members of the src family, the protein tyrosine kinase known as lyn is expressed in a broad range of cell types and tissues (Bolen et al, 1992). Largely through co-precipitation studies, lyn has been shown to be physically associated with a number of haematopoietic cell surface receptors, including the B cell antigen receptor (BCR) (Yamanashi et al, 1991; Burkhardt et al, 1991; Campbell and Sefton, 1992), CD40 (Ren et al, 1994), the lipopolysaccharide (LPS) receptor (Stefanova et al., 1993), the high affinity FcεRI complex (Eiseman and Bolen, 1992), and the G-CSF receptor (Corey et al, 1994). In most cases, more than one member of the src family has been found to be associated with the same cell surface receptor, raising the possibility of functional redundancy within the src family. This notion is supported by the milder than expected phenotype shown by mice in which one or other src-related kinase genes has been disrupted by homologous recombination in embryonic stem (ES) cells (reviewed in Varmus and Lowell, 1994). However, mice in which the lyn gene is disrupted have not hitherto been described.

A competent, signal-transducing BCR consists of an antigen-binding membrane immunoglobulin (Ig) non-covalently associated with disulphide-linked heterodimers of Ig-α and Ig-β/γ subunits (Reth, 1992). While the molecules that make up this BCR complex lack intrinsic catalytic activity, stimulation of resting B cells with antibodies to membrane Ig induces rapid tyrosine phosphorylation of B cell proteins, suggesting associated tyrosine kinase activities (Gold et al, 1990; Campbell and Sefton, 1990; Gold et al, 1991). This increase in total cellular tyrosine phosphorylation is correlated with an increase in the enzymatic activity of several members of the src family, including lyn, blk, fyn, and fgr; indeed, co-immunoprecipitation studies have shown a physical association between the BCR complex and several members of the src family (Yamanashi et al, 1991; Burkhardt et al, 1991; Campbell and Sefton, 1992; Wechsler and Monroe, 1995). A highly conserved motif, termed the immunoreceptor tyrosine-based activation motif (ITAM), is found in many signal transducing subunits, including the cytoplasmic domain of the Ig-α and Ig-β/γ molecules. Conserved tyrosine residues within this ITAM are a target for phosphorylation upon ligation of the BCR, and presumably provide docking sites for additional molecules involved in B cell signalling, such as PI 3-kinase, PLC-γ2 and GTPase-activating protein. Recent studies have shown that the cytoplasmic domain of the Ig-α chain is constitutively associated with the src family kinases lyn and fyn (Clark et al, 1992; Pleiman et al., 1994a). This suggests that members of the src family may directly phosphorylate the ITAMs, and thus participate in very early events in the BCR signal transduction cascade.

Signalling events from the BCR resemble those thus far characterised for the FcεRI complex (Ravtetch, 1994). FcεRI is a tetrameric structure consisting of a ligand binding α subunit, a β subunit and homodimeric γ subunits (Blank et al, 1989). Like the Igα and Igβ/γ signalling molecules of the BCR complex, the cytoplasmic domains of the β and γ subunits of FcεRI also contain ITAMs (Ravetch, 1994). Biochemical studies have shown that lyn is associated with the β subunit, and it is thought that on FcεRI triggering, lyn becomes activated and phosphorylates critical tyrosine residues in the ITAMs of both the β and γ subunits. The phosphorylation of the γ subunit recruits and activates p72syk, which in turn activates other molecules involved in the signal transduction cascade (reviewed in Ravetch, 1994).

To gain an insight into the physiological role of lyn and to gauge its importance in relaying signals from these different cell surface receptors, we have generated mice which are unable to express lyn (lyn –/– mice) by gene targeting in ES cells. Our results show that lyn is an indispensable component of the BCR and FcεRI complexes, and that its actions are required for the elimination of autoreactive antibodies. In addition, our longitudinal studies of lyn –/– mice show that the absence of the lyn gene is associated in the long term with depletion of lymphoid tissue, extramedullary haematopoiesis, expansion of cells of the myeloid lineage, glomerulonephritis leading to renal failure, and lesions in spleen, lymph node, liver and kidney resembling malignancy. Consequently the lyn –/– mouse is useful as a model of autoimmune disease, especially autoimmune glomerulonephritis, and of certain malignancies or dysplasias of myeloid origin, such as myeloid leukemia, malignant histiocytoma, and histiocytosis.

SUMMARY OF THE INVENTION

According to one aspect of the invention there is provided a non-human animal carrying a disruption of a gene encoding a lyn protein tyrosine kinase.

Preferably the animal is a rodent, for example a mouse, rat, rabbit or hamster, and more preferably is a mouse.

Preferably spleen or liver cells of the animal are incapable of producing detectable levels of enzymically-active lyn. Also preferably the gene encoding lyn is completely inactivated. Most preferably the animal carries a mutation directed to deletion of the lyn promoter and associated regulatory sequences. Even more preferably, the deletion comprises the region between an PstI site upstream of the lyn promoter and XbaI site approximately 11.5 kB downstream in intron 1 of the lyn gene.

Optionally the animal may also carry one or more additional mutations which result in disruption of a specific gene. For example, another protein tyrosine kinase of the src family may be disrupted; alternatively, a gene encoding a cytokine such as an interleukin, a receptor such as the B-cell antigen receptor, the lipopolysaccharide receptor, the high affinity FcεRI complex, or the GSF receptor, or a growth factor, such as G-CSF, is disrupted. Such animals bearing double or multiple targeted gene disruptions (double or multiple knock-out animals) can be generated by crossing animals in which the gene encoding lyn is disrupted with animals in which the other desired gene(s) is disrupted. Alternatively, animals in which the gene encoding lyn is disrupted can be crossed with animals in which there is a naturally-occurring mutation which affects immune function. Mice in which the genes for GM-CSF and/or G-CSF are disrupted are described in Patent Application No. WO/9523862 (PCT/AU94/00103); other suitable mouse strains, both generated by targeted gene disruption or naturally-occurring, are described herein, or are known in the art.

According to a second aspect, the novel animals of the invention, especially mice, provide a convenient model system for the study of diseases associated with or caused by lyn deficiency, and for the testing of putative therapeutic agents for the treatment or prevention of these diseases. It is contemplated that these diseases include, but are not limited to, autoimmune diseases, allergy and asthma, and malignant disease.

In one embodiment, this aspect of the invention provides a model system for autoimmune disease, especially autoimmune disease manifested by glomuleronephritis and/or pancytopaenia; also preferably the animal is a lyn −/− mouse of more than six weeks of age.

In an alternative embodiment of this aspect, the invention provides a model of malignant disease of cells of the myeloid lineage; preferably the malignant cells are myelo/monocytic or histiocytic in appearance.

The person skilled in the art will recognise that such animals presenting models of disease provide a suitable system in which to test putative therapeutic agents for treatment or prevention of these diseases. Suitable therapeutic agents for testing in this system include analogues or fragments of lyn which have protein tyrosine kinase activity. The skilled person will also appreciate that gene therapy to provide the lyn gene may be the most appropriate course. Methods for such gene therapy are known in the art, given that the identity of the defective gene is known and that the appropriate DNA has been isolated. In a particularly preferred form, it is contemplated that intravenous administration of liposomal formulations of cDNA encoding lyn will be used, as described for example by Zhu et al (1993). A variety of viral vectors for use in gene therapy is known in the art. For example, replication-incompetent adenovirus, adeno-associated virus, herpesvirus, and retrovirus vectors have been used. In addition, in at least some situations bare DNA can be injected or applied directly.

In a further aspect the invention provides a method of diagnosis of a disease associated with or caused by lyn deficiency, comprising the step of testing a tissue or cell sample from a subject suspected of suffering from such a deficiency for the absence of the gene encoding lyn. The test may suitably be carried out using peripheral blood lymphocytes, but may also use tissue obtained by biopsy, for example from kidney, liver or spleen. Such tests may be carried out using methods known per se, such as protein kinase assay, polymerase chain reaction, or reaction with a probe labelled with a detectable marker, for example using in situ hybridization. It is contemplated that this diagnostic method of the invention will be particularly useful in the differential diagnosis of autoimmune disease, cancer, allergy and asthma.

The animals of the invention have been shown to have a defective IgE-mediated anaphylactic response. The invention therefore provides a method of prevention or amelioration of an IgE-mediated immune reaction, comprising the step of administering to a subject in need of such treatment an effective dose of an antagonist of lyn.

As will be discussed in detail below, we have surprisingly found that mice in which lyn expression is disrupted show significant depletion of lymphoid tissue accompanied by extramedullary haematopoiesis with increasing age; these changes are accompanied by increased ability of bone marrow cells to form haematopoietic colonies in semi-solid agar culture. These results, coupled with the incidence of apparent malignancy in spleen, lymph node, liver and kidney of these aged mice suggests either that there is a loss of control of one or more growth factors, or that a hitherto unknown growth factor is present.

Thus in yet a further aspect the invention provides a factor which is involved in regulation of haematopoiesis, and which is present in animals in which expression of lyn is disrupted. As is well known in the art, such haematopoietic growth factors in mice have a high degree of homology with the corresponding factors in humans, and this homology is sufficient to enable a gene encoding a murine growth factor to be used as probe for the isolation of the corresponding human factor. Even if the degree of homology is relatively low, iterative screening at low stringency can be used. Therefore this aspect of the invention also provides a gene encoding a factor involved in regulation of haematopoiesis, and which is present in animals in which the expression of lyn is disrupted, which can be used for isolation of the corresponding human gene.

In a final aspect, the invention provides a targeting construct for disruption of the gene encoding lyn, as described herein.

(A) Targeting vector and homologous recombination at the lyn locus. A partial restriction map of a portion of the lyn locus is shown; the filled box represents the mouse lyn promoter. The arrow represents the direction of transcription of PGKNeo. The locations of diagnostic PCR primers 1 and 2 and the probe used for Southern analysis are indicated. Wavy lines indicate plasmid sequences. The predicted map of the mutated lyn allele is shown at the bottom. B, BamHI; N, NcoI; H, HindIII; P, PstI; X, XbaI. Not all PstI sites are indicated.

(B) Representative Southern blot analysis of progeny from a heterozygote cross. Tail DNA was digested with NcoI and probed with the diagnostic probe shown in (A). The genotype of each animal is shown above the corresponding lane, and is lyn +/+, (wild type), lyn +/− (heterozygote), and lyn −/− (homozygous mutant). The size in kb is indicated on the left.

(C) PCR using pairs of primers specific for mouse lyn or hck on reverse transcribed liver RNA from lyn +/+, lyn +/− and lyn −/− mice. The size in bp is indicated on the left.

(D) Immunoprecipitation and kinas,e assay on liver and spleen extracts of lyn +/+, lyn +/− and lyn −/− mice. Extracts were immunoprecipitated with either preimmune sera (P) or anti-lyn antisera (I) and subjected to kinase assay. Phosphorylated products were separated on 10% polyacylamide gels and revealed by autoradiography. The extracts were not equated for protein concentration. The relative molecular weight in kD is indicated on the left.

Figure 2A:
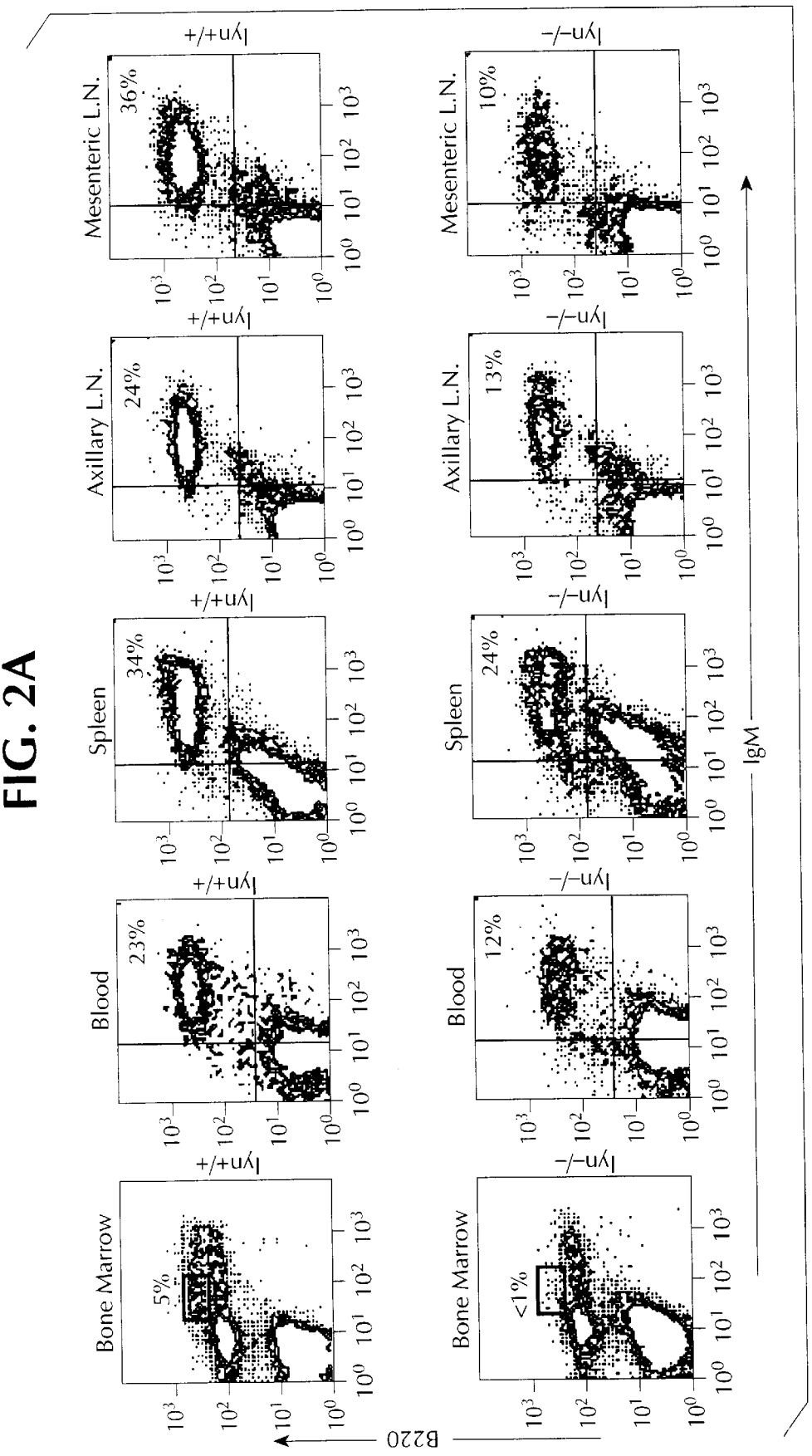
Figure 2B:
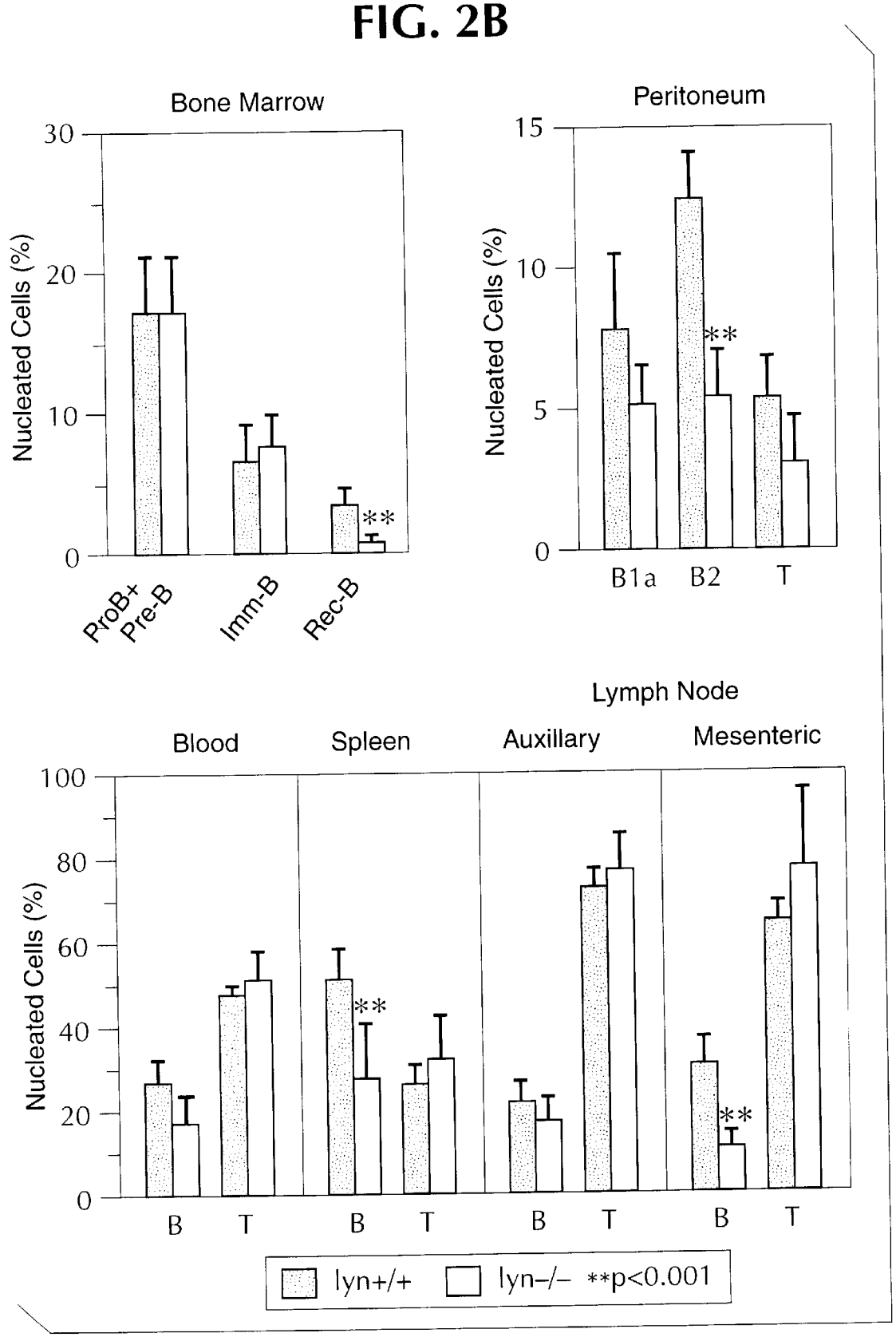

FIGS. 2A–2B shows that Lyn −/− mice have lower levels of recirculating B cells.

(A) Representative two-colour fluorescence analysis of lymphoid tissues from lyn +/+ and lyn −/− mice, stained using mAbs to B220 and IgM. The boxes in the bone marrow profiles show the % of recirculating B cells; the % of B cells present in other tissues are indicated.

(B) Left panel: proportion of $B220^{lo}/CD43^+/IgM^-$ (or pro-B), $B200^{lo}/CD43^-/IgM^-$ (or pre-B), (proB & preB), immature B (Imm. B) and recirculating B (Rec. B) cells in the marrows of lyn +/+ mice (solid bars) and lyn −/− mice (open bars). The results are derived from the analysis of marrows from 8 mice by two-colour fluorescence using mabs to B220 and IgM. The average number of nucleated cells recovered from lyn +/+ and −/− marrows were $1.95 \times 10^7 \pm 0.3 \times 10^7$ and $2 \times 10^7 \pm 0.4 \times 10^7$ respectively.

Middle panel: Proportion of B (B) and T (T) cells in lymphoid tissues from lyn +/+ mice (solid bars) and lyn −/− mice (open bars) enumerated using mabs to B220 and CD5 respectively. Numbers of mice used in the analysis: blood (4), spleen (16), axillary lymph node (10), mesenteric lymph node (16). The average numbers of nucleated cells recovered from lyn +/+ and lyn −/− mice were: blood, lyn +/+ $8.7 \times 10^6 \pm 0.6 \times 10^6$, lyn −/− $7 \times 10^6 \pm 0.4 \times 10^6$; spleen, lyn +/+ $1.5 \times 10^8 \pm 0.3 \times 10^8$, lyn −/− $1.2 \times 10^8 \pm 0.1 \times 10^8$; axillary lymph node, lyn +/+ $10^7 \pm 0.3 \times 10^7$, lyn −/− $1.3 \times 10^7 \pm 0.45 \times 10^7$; mesenteric lymph node, lyn +/+ $2.8 \times 10^7 \pm 0.4 \times 10^7$ lyn −/− $2.4 \times 10^7 \pm 0.8 \times 10^7$ Right panel: Proportion of $Ly-1^+$ B cells (B1a), conventional B cells (B2) and T cells (T) in the peritoneal cavity of lyn +/+ mice (solid bars) and lyn −/− mice (open bars). Results are derived from the analysis of peritoneal cells from 5 mice by three-colour fluorescence, using mabs to B220, CD5 and IgD. The average numbers of nucleated cells recovered from lyn +/+ and −/− peritoneum were $5.4 \times 10^6 \pm 2.2 \times 10^6$ and $7.3 \times 10^6 \pm 2.7 \times 10^6$ respectively.

** indicates statistical significance, $p<0.001$ using Student's t-test. Data are represented as mean±SD.

FIGS. 3A–3E shows representative results of analysis of B and T cell function in Lyn −/− mice.

(A) Mesenteric lymph node cells from lyn +/+ (solid bars) or lyn −/− mice (hatched bars) were cultured for 3 days in the presence of medium, lipopolysaccharide (LPS) or anti-Ig. DNA synthesis was measured by pulsing with ($^3$H) thymidine for 6 hr. A representative result of one out of six experiments is shown.

(B) Splenocytes from lyn +/+ (solid bars) or lyn −/− mice (hatched bars) were cultured for 3 days in the presence of medium, anti-Ig or LPS. DNA synthesis was measured by pulsing with ($^3$H) thymidine for 6 hr. A representative result of one out of six experiments is shown.

(C) Lymph node and spleen cells from lyn +/+ (solid bars) or lyn −/− mice (hatched bars) were cultured on mitotically inactivated fibroblasts expressing CD40 ligand for 3 days. Cultures were pulsed with ($^3$H)thymidine for 6 hr. A representative result of one out of three experiments is shown.

(D) Mesenteric lymph node cells from lyn +/+ (solid bars) or lyn −/− mice (hatched bars) were cultured for 3 days in the presence of medium or the T cell mitogen ConA. DNA synthesis was measured by pulsing with ($^3$H)thymidine for 6 hr. A representative result of one out of three experiments is shown.

(E) One-way mixed lymphocyte reaction using mitotically inactivated stimulator spleen cells from either BALB/c allogeneic mice (allo MLR) or syngeneic mice (auto MLR). Responder cells were derived from lymph nodes of lyn +/+ (solid bars) or lyn −/− mice (hatched bars). A representative result of one out of two experiments is shown.

Data are represented as mean±SD.

Figure 4A:
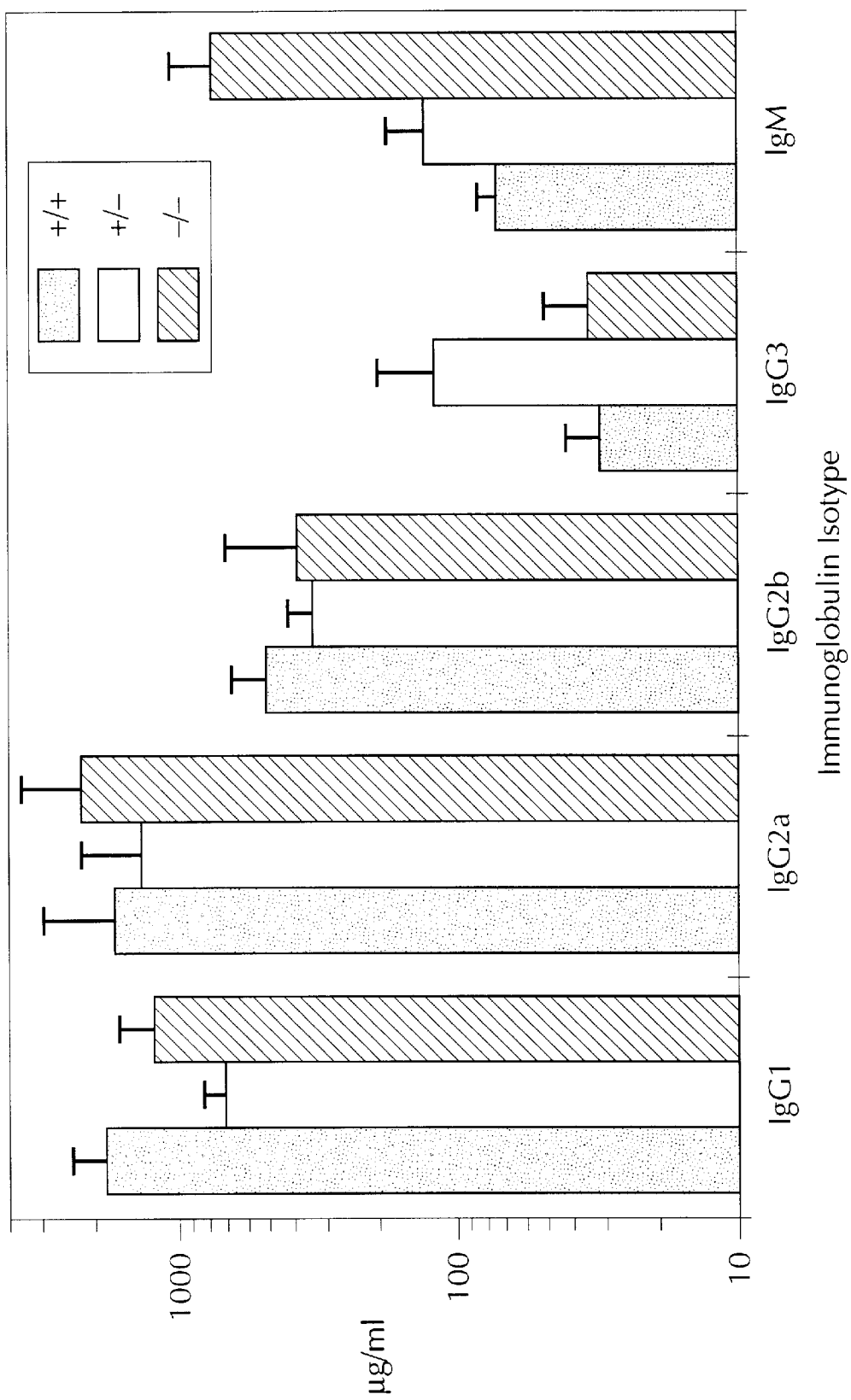
Figure 4B:
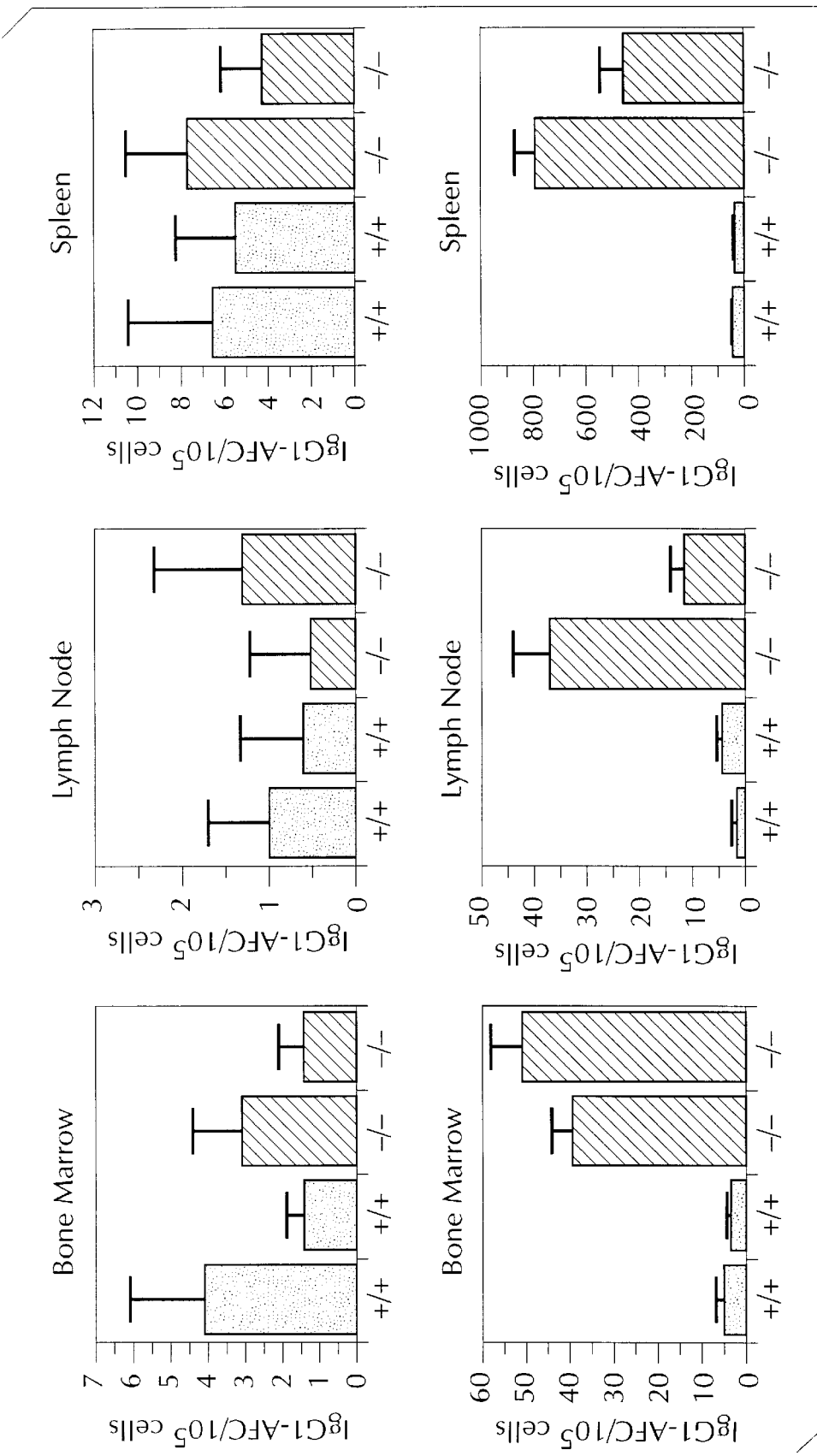

FIGS. 4A–4B shows the levels of immunoglobulin (Ig) in the serum of unchallenged mice and the frequency of IgG1 and IgM secreting cells.

(A) Levels of Ig isotypes in the serum of a cohort of six lyn +/+ (solid bars), lyn +/− (open bars) and lyn −/− (hatched bars) mice, as determined by ELISA. Data are represented as the geometric mean±SD.

(B) ELISPOT was used to determine the frequency of IgG1- and IgM-Antibody forming cells in suspensions of bone marrow, mesenteric lymph node and spleen prepared from two lyn +/+ (solid bars) and two lyn −/− (hatched bars) mice. Data are represented as mean±SD of eight replicate wells per sample. A representative result of one out of three experiments is shown.

Figure 5A:
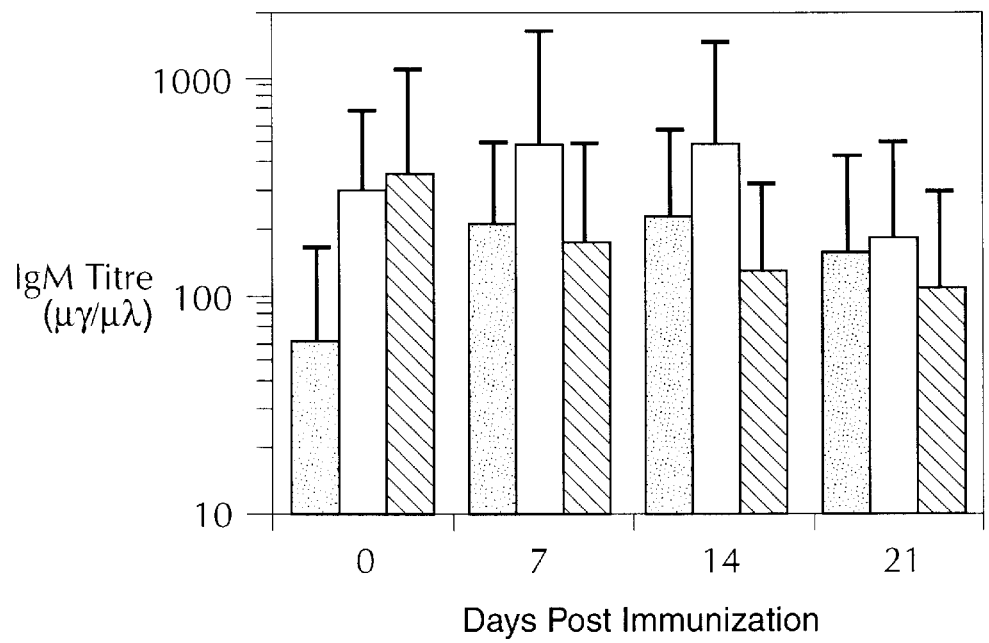

FIGS. 5A–5B illustrates the immune response of Lyn −/− mice after challenge with TI and TD antigens.

(A) IgM (i) and IgG3 (ii) response of a cohort of lyn +/+ (solid bars), lyn +/− (open bars) and lyn −/− (hatched bars) mice at the indicated times after immunization with 10 μg of (4-hydroxy-3-nitrophenyl) acetyl (NP) coupled to LPS.

(B) IgM (i) and IgG1 (ii) response of a cohort of lyn +/+ (solid bars), lyn +/− (open bars) and lyn −/− (hatched bars) mice at the indicated times after immunization with 100 μg of NP coupled to keyhole limpet haemocyanin (KLH). Data are represented as geometric mean±SD.

FIGS. 6A–6M shows lymph node histology, kidney pathology and autoantibodies in control and Lyn −/− mice.

(A) Low-power view of a lymph node from a control mouse, showing well-formed secondary follicles with germinal centers (arrow).

(B) Low-power view of a lymph node from a lyn −/− mouse, showing poorly-formed follicles (indicated by arrows).

(C) High-power view of the renal cortex from a control mouse, showing a normal glomerulus.

(D) High-power view of the renal cortex from a lyn −/− mouse showing an abnormal glomerulus with hypercellularity, lobularity and segmental sclerosis.

(E) High-power view of the renal cortex from a lyn −/− mouse, showing severely damaged glomeruli with global sclerosis and crescent formation.

(F) High-power view of periodic acid silver methenamine (PAS-M)-stained section through the renal cortex of a control mouse, showing normal single contour of peripheral capillary loop basement membrane.

(G) High-power view of PAS-M-stained section through the renal cortex of a lyn −/− mouse, indicating mesangial interposition, which is seen as tram-tracking or double contours of the peripheral capillary loop (arrows).

(H) View of the renal cortex from a control mouse stained with a pool of goat anti-mouse IgGs, indicating a lack of immune complexes (magnification×250).

(I) View of the renal cortex from a lyn −/− mouse, showing IgG-containing immune complexes in glomeruli (magnification×250).

Immunofluorescent analysis of human HEp-2 cells (Moore et al, 1995) stained with antisera from (J) a control mouse and different lyn −/− mice (K–M) (magnification× 250).

Figure 7:

FIG. 7 shows the rapid passive cutaneous anaphylaxis (PCA) reaction as visualised by Evans blue extravasation in control mice whereas Lyn −/− mice failed to mediate this response.

DETAILED DESCRIPTION OF THE INVENTION

The invention will now be described in detail by way of reference only to the following examples, and the accompanying drawings.

Experimental Procedures
Reverse Transcription and PCR Amplification

A pair of primers specific for mouse lyn (5'-ATGGGGAATGGTGGAAAGCT(SEQ ID NO:1) and 5'-ACTTCCCCAAACTGCCCTGC)(SEQ ID NO:2) was used to assess whether the lyn gene was expressed in mice carrying a mutation in their lyn promoter. Primers specific for mouse hck (5'-CTGGGGGGTCGGTCTAGCTGC(SEQ ID NO:3) and 5'-GGTATCCTCAGAGCCCTCCAC)(SEQ ID NO:4) were used as a positive control. The reverse transcription reaction was carried out using a GeneAmp RNA PCT Kit (Perkin Elmer Cetus, Norwalk, Conn.) according to the manufacturer's instructions on 1 $\mu$g RNA derived from mouse liver, using oligo (dT) as the 3' primer. Following reverse transcription of RNA, PCR amplification of cDNA was carried out by sequential cycling for 35 cycles at 95° C. (30s), 60° C. (30s) and 72° C. (30s). Products were electrophoresed on 1% agarose gels.

Immunoprecipitation and Kinase Assays

Spleen and liver extracts were prepared, immunoprecipitated with preimmune or lyn-specific antisera and subjected to kinase assay as previously described (Stanley et al, 1991).

Flow Cytometric Analysis

Bone marrow cells were obtained by flushing femurs, and peritoneal cavity cells were isolated by peritoneal lavage using PBS/1% FBS. Peripheral blood (0.2 ml) was depleted of red blood cells by using 0.83% $NH_4Cl$ prior to staining. Single cell suspensions were prepared from lymphoid organs in PBS/1% FBS. Cells ($10^5$) were incubated with fluorescein (FITC)- and phycoerythrin (PE)-conjugated monoclonal antibodies (mAbs), and analysed using a FACScan (Becton-Dickinson, San Jose, Calif.). For three-colour analysis, a biotinylated antibody revealed with TriColor Avidin (Caltag, So. San Francisco, Calif.) was used in addition to direct FITC and PE conjugates. Dead cells were excluded on the basis of propidium iodide uptake and 10,000 events were acquired. The following mAbs were used: RA3-6B2 (B220), 331.12 (IgM), goat anti-mouse IgD (Nordic Immunological Laboratories, Tilburg, The Netherlands), 187.1 (IgK), JC5 (Ig$\lambda$), S7 (CD43), B3B4 (CD23), M1/69 (HSA), M5/114 ($Ia^{b,d}$), GK1.5 (CD4), 53.6 (CD8), 53.7 (CD5), M1/70 (CD11b), 6B2-8C5 (GR-1), and Mel-14 (L-selectin).

Proliferation Assays

Cells were cultured at a density of $5\times10^5$ B cells per ml in complete RPMI medium. Anti-Ig stimulation was performed using a F(ab')$_2$ goat anti-mouse IgM (Capella, Durham, N.C.) at a final concentration of 25 $\mu$g/ml. LPS (Difco, Detroit, Mich.) was used at a final concentration of 20 $\mu$g/ml. CD40 ligand-transfected 3T3 fibroblasts were generated using standard techniques, and were irradiated at 3000 rads for 20 minutes prior to culture. $^3$H thymidine (10 $\mu$Ci) was added to the cultures on the indicated days, and the cells were harvested 6 hrs later. DNA was immobilized onto filters, and the amount of $^3$H-thymidine incorporated determined using a scintillation counter (Packard Instrument Company, Meriden, Conn.).

Immunization, ELISA and ELISPOT Assays

NP-KLH (100 $\mu$g in alum) and NP-LPS (10 $\mu$g in PBS), prepared as previously described (Lalor et al, 1992), were administered by intraperitoneal injection. Serum titres of antigen-specific Ig of the indicated isotypes were determined at regular intervals after immunization, using an NP-specific ELISA performed as previously described (Smith et al, 1994). Total serum Ig titres were determined by ELISA using sheep anti-mouse Ig (Silenus Laboratories, Hawthorn, Australia) as a capture reagent, and developed with isotype-specific goat sera directly conjugated with horseradish peroxidase (Southern Biotechnology Associates Inc., Birmingham, Ala.). Purified myeloma proteins (Sigma Chemical Co., St. Louis, Mo.) were used as standards. ELISPOT assays were carried out as previously described (Lalor et al, 1992), again using sheep anti-mouse Ig capture and goat anti-mouse Ig developing reagents as described above.

Immunohistochemistry and Immunofluorescence

Anti-nuclear antibodies were detected using fixed human HEp-2 cells (Immuno-Concepts, Sacramento, Calif.), following the manufacturer's instructions. Sera from lyn +/+ and −/− mice were used at a dilution of 1:100 and 1:1000 respectively. Bound antibodies were revealed with a fluoresceinated sheep anti-mouse Ig serum (Silenus Laboratories). Frozen sections of kidneys were prepared and stained as previously described (Smith et al, 1994). Immune complexes were detected by staining with a pool of IgG1-, IgG2a-, and IgG2b-specific sera directly conjugated to horseradish peroxidase (Southern Biotechnology Associates Inc.).

Histology

Tissues were fixed for light microscopy in either formalin or Bouin's solution for 24 hr and embedded in paraffin. Sections were stained with haematoxylin and eosin, periodic acid silver methenamine (PAS-M), or Alcian blue, according to standard procedures. Sections for electron microscopy were prepared following fixation in 2.5% glutaraldehyde, post-fixing in osmium tetroxide, embedding in Spurr's resin and staining with lead citrate.

Passive Cutaneous Anaphylaxis

Control and lyn −/− mice were anaesthetised with chloral hydrate, then injected intradermally in their left ears with 20 ng mouse anti-dinitrophenyl (anti-DNP) IgE antibody (Sigma) diluted in 20 $\mu$l of PBS. The right ears of the same mice were injected with PBS. After 24 hr, the mice were given an intravenous injection of 100 $\mu$g of DNP-human serum albumin (HSA) (Sigma) in 100 $\mu$l of 0.9% NaCl/1% Evans blue dye. The PCA reaction was evident within 5 min of the second injection, and after 60 min mice were sacrificed and their ears subjected to histological analyses.

EXAMPLE 1

Derivation of Lyn −/− Mice and Verification of Gene Disruption

Generation of Lyn −/− Mice

Figure 1A:
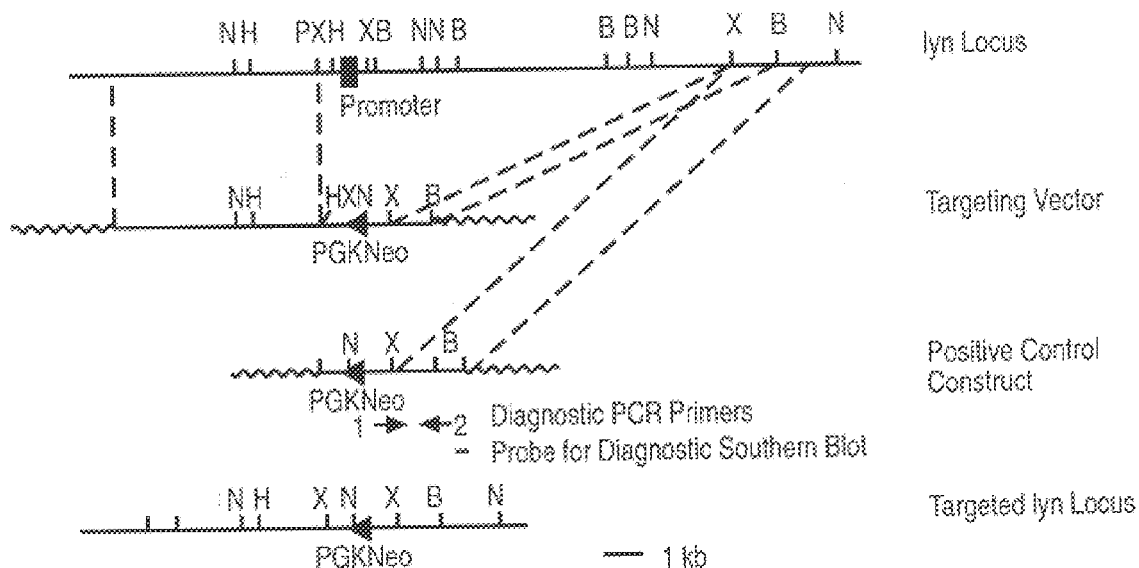
FIGS. 1A–1D illustrates the generation of Lyn null (lyn −/−) mice.

Genomic clones containing the mouse lyn promoter have been described previously (Hibbs et al, 1995), and were used to construct the targeting vector. Initial attempts to create lyn −/− mice were frustrated by the discovery that a significant portion of the coding sequences of the lyn gene is duplicated. Structural analysis revealed that the promoter and exons 11 to 13 are present in single copy; however, sequences corresponding to the first coding exon are duplicated, and this duplication extends to intron 10. Two sets of genomic clones representing the duplicated regions were isolated and characterised, and nucleotide sequence analysis showed minimal sequence divergence between the two. Southern blot analysis of DNA from various species showed that this duplication is present only in the mouse, and that otherwise the overall structure of the mouse lyn gene is similar to those of other src family members. To overcome this problem, a targeting vector was constructed to replace the lyn promoter and associated regulatory sequences (approximately 11.5 kb of genomic sequence) with a PGKNeo expression cassette. A positive control construct was generated by ligating an additional 840 bp of genomic sequence to the 3' end of the short arm of the targeting construct, and was used to develop a diagnostic PCR. The structure of this construct is shown in FIG. 1A. The pGKNeo expression cassette (Tybulewicz et al, 1991) was inserted in reverse transcriptional orientation to the lyn gene between a PstI site upstream of the promoter and an XbaI site approximately 11.5 kb downstream in intron 1, creating a construct with a long arm of homology of 5.3 kb and a short arm of 1.1 kb in length.

E14 ES cells (Handyside et al, 1989) were propagated and electroporated as previously described (Mann et al, 1993). Selection for growth in G418 was initiated 24 hr after electroporation, and G418-resistant colonies were micro-manipulated after a further 7 days. Twenty percent of the cells comprising an individual colony were replated into a well of a 96-well plate containing mitotically-inactivated STO cells, and were used as a stock; the remaining 80% of cells were replated and cultured for a further 4 days, after which DNA was prepared from pools of two or four clones. Following electroporation of the targeting construct into E14 ES cells, a polymerase chain reaction(PCR)-based screening assay was employed to screen 720 pools. PCR reactions were carried out using 1 µl of the DNA sample in the presence of 2.0 mM $MgCl_2$ using Tth plus DNA polymerase (Biotech International, Bentley, Western Australia). PCR products were generated by 35 cycles at 95° C. (30 s), 60° C. (30 s) and 72° C. (90 s) respectively. Of the primers used to identify homologous recombinants, primer 1 was complementary to sequences at the 5' end of the PGK promoter (5'-dTGCTACTTCCATTTGTCACGTCC-3')(SEQ ID NO:5), and primer 2 was complementary to lyn genomic sequences downstream of the short arm of homology (5'-dACAGAGCTAGACCGTTCTTTCCTC-3')(SEQ ID NO:6) as shown in FIG. 1A. A third primer was used in combination with primer 2 to identify the wild type lyn allele (5'-dCAGGTGGAGCATACCTGGCTGTTT-3')(SEQ ID NO:7).

DNA from two pools generated a PCR product whose size was predicted following homologous recombination of the targeting vector and the lyn gene. On the basis of Southern analysis using a probe corresponding to sequences external to the targeting construct as well as a neo probe, two clones, designated lyn20.4 and lyn81.1, were established.

These two targeted ES cell clones were injected into blastocysts of C57BL/6 mice and transplanted into the uteri of pseudopregnant females. Following injection of targeted ES cells into C57BL/6 blastocysts, chimeras were generated, although only lyn81.1 cells were able to transmit the disrupted lyn locus through the germ-line. Chimeric animals were mated with C57BL/6 mice, and germ-line transmission of the mutated lyn allele was confirmed by Southern analysis of NcoI digested genomic DNA, using probes directed to lyn genomic sequences outside the targeting vector (FIG. 1A) and to the neor gene.

Figure 1B:
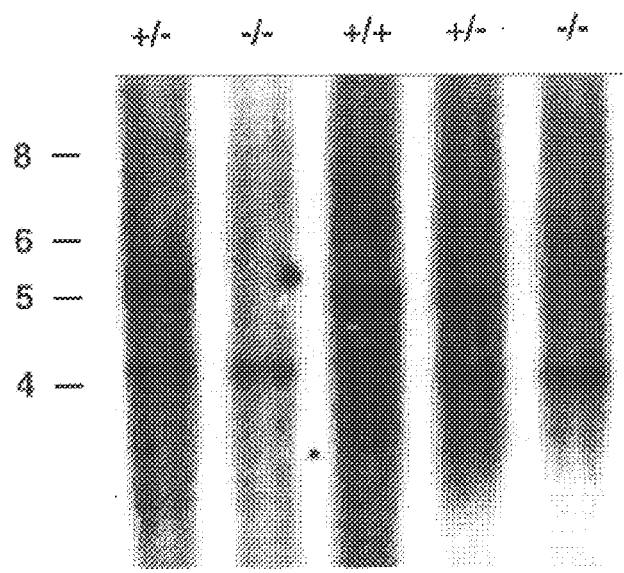

Lyn +/− animals were interbred to produce litters that included lyn −/− offspring. Southern blot analysis of mouse tail DNA from progeny derived from such a mating identified the expected three genotypes, as shown in FIG. 1B, and these were in a ratio consistent with normal patterns of Mendelian inheritance (158 lyn +/+, 292 lyn +/−, 130lyn −/−). The mutant mice were viable and fertile, and young mice were superficially healthy. Mice were maintained in a conventional animal facility.

Figure 1C:
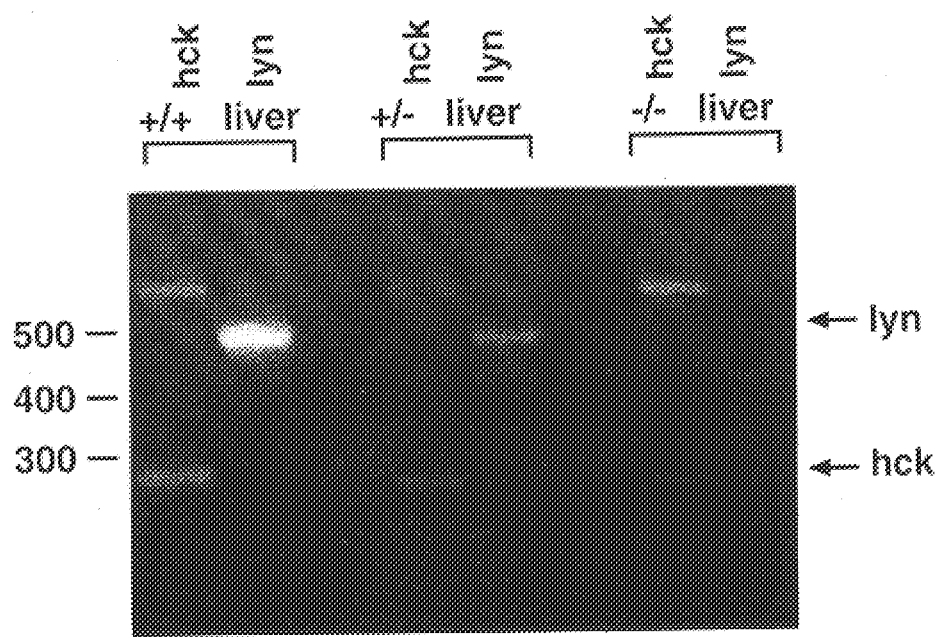
Figure 1D:
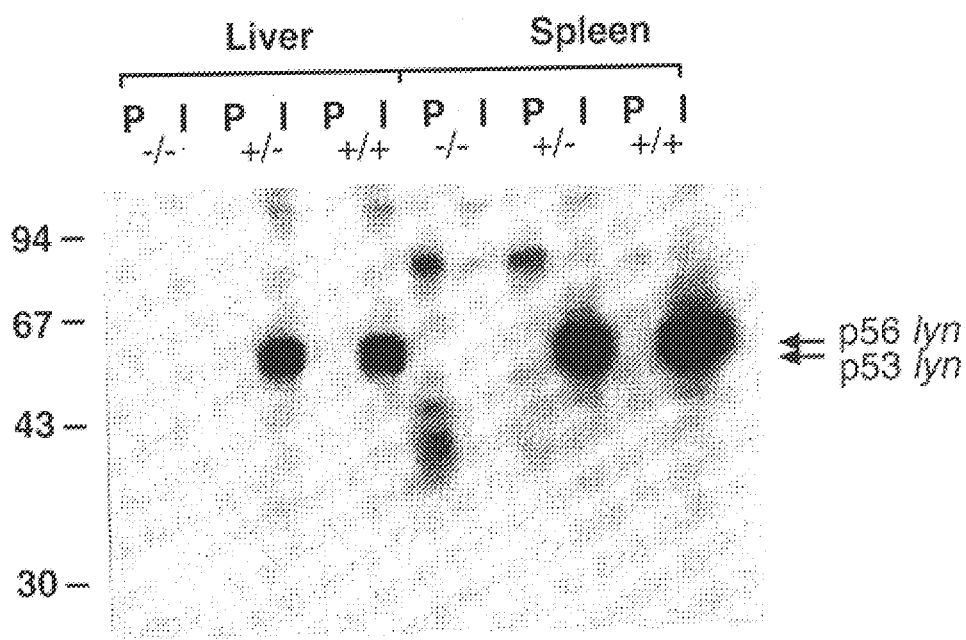

To verify that the targeted lyn gene was not expressed, PCR was performed on reverse-transcribed mRNA derived from mouse livers, using lyn-specific oligonucleotide primers (Hibbs et al, 1995). The expected 495 bp lyn-related PCR product was only generated using mRNA originating from lyn +/+ and +/− mice (FIG. 1C). Moreover, while we were able to detect lyn tyrosine kinase activity in spleen and liver extracts from lyn +/+ and +/− animals, none was detected in extracts prepared from lyn −/− animals, as illustrated in FIG. 1D.

EXAMPLE 2

Lyn −/− Mice have Reduced Numbers of Recirculating B Cells

The only discernible effect of the Lyn null mutation on leukocyte development in young animals was observed in the B lymphocyte lineage. Changes in the B cell lineage were investigated by flow cytometric analyses of lymphoid tissues, using mAbs to the pan-B cell marker B220 in combination with an array of mAbs specific for developmentally regulated markers. The profiles of lyn +/− mice and lyn +/+ mice were indistinguishable. The sizes of the pro-B ($B220^{lo}/CD43^+/IgM^-$), pre-B ($B220^{lo}/CD43^-/IgM^-$) and immature B ($B220^{lo}/CD43^-/IgM^+$) cell populations were the same in lyn +/+ and −/− bone marrow. The recirculating B cell ($B220^{hi}/CD43^-/IgM^+$) population in lyn −/− bone marrow, however, was reduced by between 50% and 100% compared to controls, as shown in FIG. 2. A reduction in the total number of $B220^+/IgM^+$ cells was also observed in secondary lymphoid tissues from the lyn −/− mice, although again some variation was noted between mice and, somewhat surprisingly, between tissues. Mesenteric lymph nodes always showed a greater reduction of B cells than the spleen and other lymph nodes from the same animal. Intriguingly, lymph nodes from the axilla and groin showed a less pronounced reduction in B cells, possibly reflecting the extent to which these organs are activated. While there was also a reduction in B cells in the peripheral blood of lyn −/− mice, this was not statistically significant (FIG. 2A and B). Conventional B cells (B2), but not Ly-$1^+$ B cells (B1a), were markedly reduced in the peritoneal cavity of lyn −/− mice (FIG. 2B). The Peyer's patches in lyn −/− mice were considerably smaller, and in some instances were microscopically undetectable. It is noteworthy that the percentage differences in B cells in lyn −/− mice reflect differences in absolute B cell number, as the average numbers of nucleated cells derived from the organs of lyn +/+ or −/− mice were essentially the same (refer to FIG. 2 legend).

The reduction in B cell numbers was not due to a selective block in B cell development, as the proportion of peripheral B cells expressing B cell developmental markers such as MHC Class II, surface IgD, CD23, heat stable antigen and Mel-14 was the same in lyn −/− and control mice.

No significant differences in the T cell composition of both primary and secondary lymphoid tissues from lyn −/− mice were noted, and T cell subsets in the thymus were normal. In secondary lymphoid tissue, there was a slight increase in the proportion of T cells, probably as a direct result of a corresponding decrease in B cells in the same tissue (FIG. 2B).

EXAMPLE 3

B Cell Function is Impaired in Lyn -/- Mice

Figure 3A:
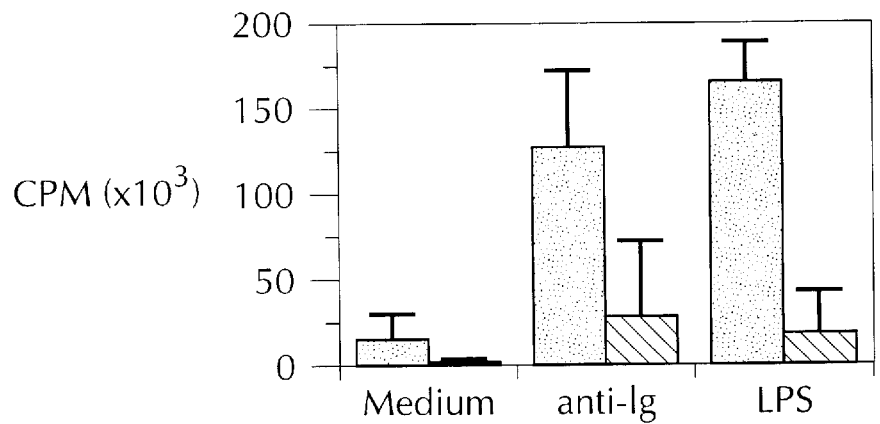

The reduction in numbers of recirculating B cells in lyn -/- mice suggests that there is a defect in their ability either to proliferate or to persist in the periphery. To distinguish between these possibilities, the proliferative potential was measured of B cells derived from the axillary lymph node, mesenteric lymph node or spleen in a $^3$H incorporation assay following stimulation of cultures with either LPS or anti-Ig. The results of representative experiments are shown in FIG. 3A. Axillary lymph nodes showed little difference between lyn +/+ and -/- mice in B cell number, while differences in B cell numbers between spleen and mesenteric lymph node were two-fold and three-fold respectively (FIG. 2B). To compensate for these differences, cultures were adjusted to contain equivalent numbers of B cells. While lymph node (FIG. 3A) and splenic B cells (FIG. 3B) from control mice responded typically to cross-linking of surface Ig with anti-Ig, the corresponding cells from lyn -/- mice responded poorly (FIG. 3A and 3B), and no alteration in the kinetics of the response was evident.

Figure 3B:
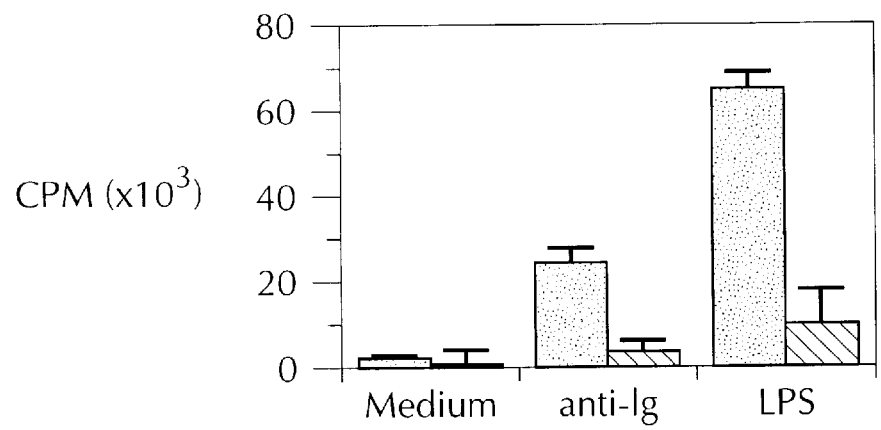

The signalling pathway linked to surface Ig appears to be distinct from that involving LPS activation, as anti-Ig induced B cell proliferation has been shown to require CD45 (Kishihara et al, 1993) and vav (Tarakhovsky et al, 1995); Zhang et al, 1995) expression, while LPS activation is independent of both these markers. To determine the relative response to LPS, equivalent numbers of lymph node (FIG. 3A) and splenic B cells (FIG. 3B) from lyn +/+ and -/- mice were assessed for their ability to respond to LPS treatment. While B cells from control animals showed a typical response, with a peak at three days, B cells from lyn -/- mice responded poorly (FIG. 3A and 3B). These data indicate that lyn is an important component of the BCR complex, and plays an indispensable role in normal B cell proliferation.

Figure 3C:
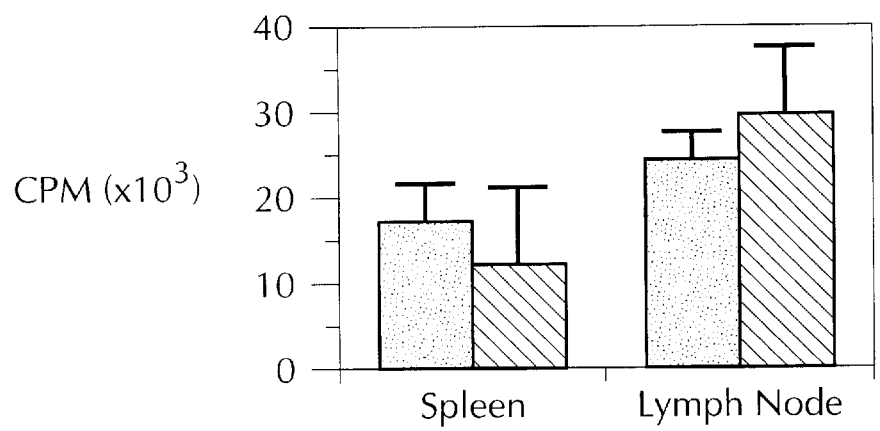

Interactions between CD40 and its ligand are pivotal in T-dependent (TD) B cell antibody responses (Banchereau et al, 1994). A recent study has shown that lyn is rapidly activated upon cross-linking of CD40 (Ren et al, 1994). To address the question of whether B cells from lyn -/- mice could respond to stimulation through CD40, spleen and axillary lymph node cells from lyn -/- and control mice were plated on mitotically inactivated NIH-3T3 fibroblasts which constitutively expressed mouse CD40 ligand. As shown in FIG. 3C, no difference was observed in the proliferative potential of splenic or lymph node derived B cells from control or lyn -/- mice, demonstrating that lyn is not crucial for signalling a CD40-mediated proliferative response.

Figure 3D:
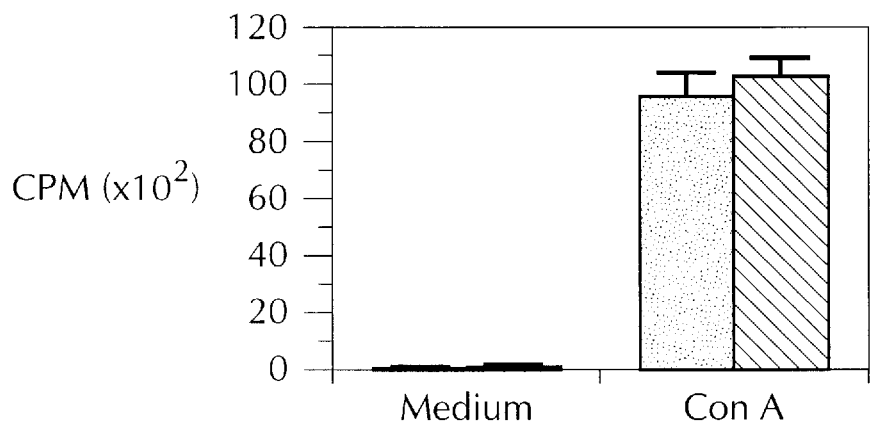
Figure 3E:
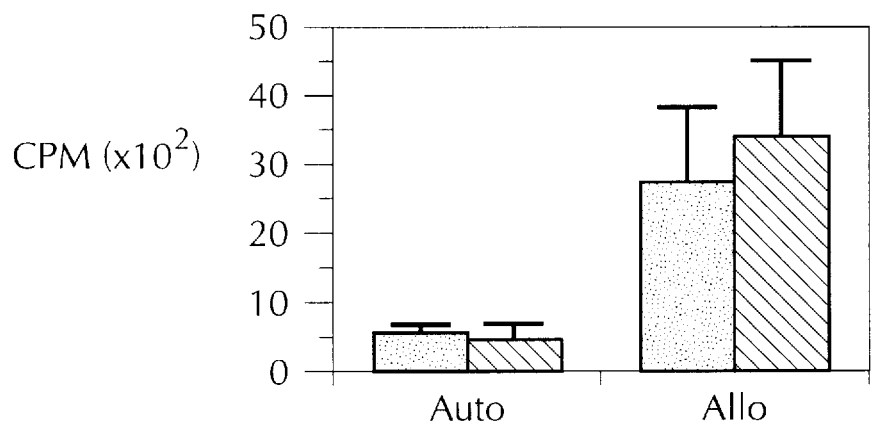

Although lyn is not expressed in normal T cells, the function of lyn -/- T cells was investigated to ensure that the aberrant B cell behaviour in the lyn -/- mice was not a consequence of impaired T cell function. No difference in proliferation in the presence of the T cell mitogen concanavalin A (ConA) was observed in lymph node T cells from lyn +/+ and -/- mice (FIG. 3D). Moreover, T cells from lyn +/+ and -/- mice, in one-way mixed lymphocyte reactions (MLR) using either autologous or allogeneic stimulator cells, were indistinguishable in their response (FIG. 3E).

EXAMPLE 4

Lyn -/- Mice have Elevated Levels of Serum IgM

The levels of Ig isotypes in the serum were measured by ELISA. As shown in FIG. 4A, Lyn -/- mice showed normal levels of circulating IgG1, IgG2a, IgG2b, and IgG3, but a ten-fold elevation in serum IgM. Lyn +/- mice had a level of IgM slightly higher than that of lyn +/+ mice, but five-fold less than that of lyn -/- mice.

An enzyme-linked immunospot (ELISPOT) assay for detection of antibody-secreting cells was used to determine whether the elevated level of circulating IgM was due to an increase in the number of antibody-forming cells (AFC). While no significant differences were observed in the number of IgG1-AFC in lyn -/- mice compared to control mice, there was a ten-fold increase in the number of IgM-AFC in all lyn -/- lymphoid tissues examined as shown in FIG. 4B. Thus the elevated level of circulating IgM in lyn -/- animals is a result of an elevation in the total number of IgM-producing plasma cells.

EXAMPLE 5

Perturbed Humoral Immune Responses in Lyn -/- Mice

Figure 5A:
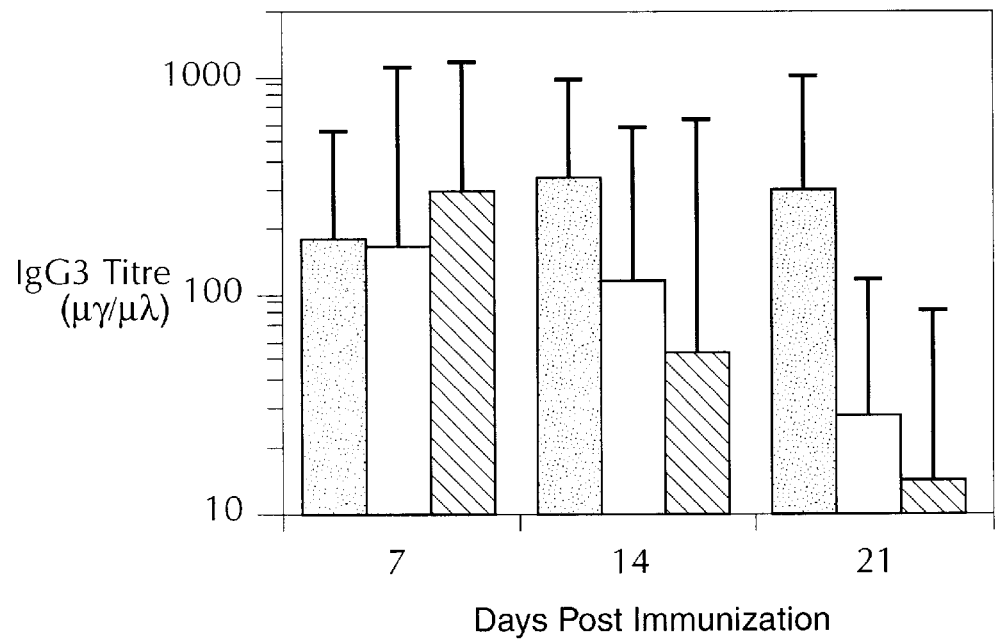

Mice challenged with T-independent (TI) antigens secrete IgM, followed by a switch to IgG3 (Coffman et al, 1993). To determine whether this response was impaired in lyn -/- mice, groups of six lyn +/+, +/- and -/- mice were immunized with 10 μg of the hapten (4-hydroxy-3-nitro-phenyl) acetyl (NP) coupled to the TI carrier LPS (NP LPS), and their serum antibody response measured weekly following immunization. The results are summarized in FIG. 5. The sera of all mice prior to immunization had measurable levels of NP-binding IgM antibodies, presumably due to high levels of circulating cross-reactive antibody (FIG. 5A, i). Although lyn -/- mice showed no measurable increase in the level of NP-specific IgM after immunization with NP-LPS, their ability to respond to this antigen was evidenced by the appearance of NP-specific IgG3 (FIG. 5A, i and ii). While lyn -/- mice mounted an efficient IgG3 response within one week of immunization, this response decayed more rapidly than that of control mice (FIG. 5A, ii). The IgG3 response of lyn +/- mice also decayed more rapidly than that of lyn +/+ mice, but was still greater than the response of lyn -/- mice. These data indicate that lyn -/- mice are incapable of sustaining normal antibody responses to TI antigens.

Challenging mice with T dependent (TD) antigens induces the rapid secretion of low affinity IgM antibodies followed by a switch to secretion of IgG, and, following somatic mutation, secretion of higher affinity antibodies (Allen et al, 1987). To determine whether TD responses were impaired in lyn -/- mice, groups of mice were immunized with 100 μg NP coupled to the protein keyhole limpet haemocyanin (KLH). Although both lyn -/- and +/- mice again had detectable levels of circulating cross-reactive IgM antibody prior to immunization, the titre increased after immunization in a manner analogous to control mice (FIG.

5B, i). Furthermore, the three groups of mice produced NP-specific IgG1 with similar kinetics, and at a similar serum titre (FIG. 5B, ii).

As shown in FIG. 6, histological sections of lymph nodes from lyn +/+ mice maintained in a conventional animal facility showed the presence of numerous germinal centres in B cell follicles (FIG. 6A). By contrast, lymph nodes from littermate lyn -/- mice show very poorly formed germinal centres, suggesting some defect in TD responses (FIG. 6B). The number of follicle centre cells was reduced, the follicles lacked zonation, and the mantle zones were poorly developed. With progressive aging, there was severe depletion of cortical lymphocytes, resulting in small atrophic lymph nodes, although plasma cells were still present within the medullary cords. Similar progressive changes were seen in the B cell zones of the splenic white pulp.

EXAMPLE 7

Lyn -/- Mice Develop Severe Glomerulonephritis as a Result of IgG Immune Complex Deposition in the Kidney A significant decline with increasing age in the numbers of lyn -/- mice compared to control mice was noted. Unlike control mice, which remained healthy, a proportion of lyn -/- mice aged from 4 weeks to 10 months became emaciated and were sacrificed. Analysis of their peripheral blood showed that all animals were severely anaemic and thrombocytopaenic (Table 1), and several were also leukopaenic. Analysis of the bone marrows of these mice indicated that the anaemia and thromrbocytopaenia was most likely due to peripheral destruction of haematopoietic cells and not to primary marrow failure, since histological examination of femoral shafts indicated that the cellularity of the bone marrow was normal in the majority of cases.

TABLE 1

Analysis of the Peripheral Blood of Control and lyn Deficient Animals

| GENOTYPE (number) | Age (weeks) | Haemoglobin (g/l) | Platelets ($\times 10^6$/ml) | WBCs ($\times 10^6$/ml) | Monocytes ($\times 10^6$/ml) |
|---|---|---|---|---|---|
| Age study** | | | | | |
| lyn +/+ (23) | 10 | 163 ± 11 | 738 ± 119 | 8.7 ± 2.7 | 0.3 ± 0.3 |
| lyn -/- (24) | 10 | 158 ± 15 | 705 ± 175 | 7.0 ± 2.2 | 0.8 ± 0.7 |
| lyn +/+ (6) | 26 | 155 ± 9 | ND | 7.5 ± 1.8 | 0.11 ± 0.1 |
| lyn -/- (6) | 26 | 138 ± 15 | ND | 11.1 ± 4.5 | 0.88 ± 1.77 |
| lyn +/+ (6) | 28 | 161 ± 5 | 918 ± 159 | 10.0 ± 2.6 | 0.12 ± 0.11 |
| lyn -/- (6) | 28 | 133 ± 17 | 567 ± 179 | 11.0 ± 5.0 | 1.02 ± 0.8 |
| lyn +/+ (6) | 30 | 147 ± 18 | 808 ± 295 | 8.1 ± 2.3 | 0.16 ± 0.37 |
| lyn -/- (6) | 30 | 106 ± 18 | 356 ± 147 | 38 ± 59 | 2.16 ± 1.05 |
| Mice with glomerulonephritis† | | | | | |
| lyn -/- (6) | 23–27 | 101 ± 34 | 420 ± 139 | 11.5 ± 6.5 | ND |
| Mice with highly enlarged spleens and glomerulonephritis† | | | | | |
| lyn -/- (7) | 28–50 | 96 ± 42 | 328 ± 182 | 60.6 ± 75.6 | ND |

*number of mice used in the analysis
ND = not determined
Data are represented as mean ± SD
**asymptomatic at time of analysis
†Mice showed clinical signs consistent with glomerulonephritis and histological evidence of glomerulonephritis

EXAMPLE 6

IgE-mediated Anaphylaxis is Defective in Lyn -/- Mice

Since lyn has been shown to be associated with the FcεRI complex, and since IgE-mediated anaphylaxis is dependent on FcεRI triggering of mast cells, we sought to determine whether FcεRI triggering is compromised in lyn -/- mice in a passive cutaneous anaphylaxis (PCA) model (Wershil et al, 1987). The results are shown in FIG. 7. Lyn +/+ (left of figure) and lyn -/- mice (right of figure) were given intradermal injections in their left ears with 20 ng mouse anti-DNP IgE diluted in PBS and in their right ears with PBS. After 24 hr, mice were injected intravenously with DNP-HSA in Evans blue. The typical PCA reaction, as indicated by extravasation of Evans blue dye, is seen in the lyn +/+ mouse's left ear, but is not evident in the corresponding ear of the lyn -/- mouse. Thus while control mice mounted a rapid PCA reaction, which is readily visualised by Evans blue extravasation due to an increase in vascular permeability as a result of mast cell degranu-lation, lyn -/- mice failed to mediate this anaphylactic response (FIG. 7). The defect reflected an impairment in mast cell function, rather than simply a reduction in mast cell numbers, as no differences in the numbers of mast cells in the ears of lyn +/+ and -/- mice was noted.

Histological examination of solid organs revealed severe renal disease, as shown in FIG. 6. Glomerular damage consisting of hypercellularity, lobularity and focal sclerosis was apparent (FIG. 6D). In some instances glomeruli were globally sclerotic; glomerular crescents were occasionally seen (FIG. 6E). In addition, mesangial interposition was present in the peripheral capillary loops (FIG. 6G). Occasional animals also showed necrotic glomerular lesions, consistent with a microcapillary vasculitis. These severe glomerulonephritic changes correlate clinically with renal failure, a probable cause for the death of some lyn -/- animals. Analysis of the kidneys from apparently healthy lyn -/- mice of 6 weeks of age showed variable, but less severe glomerular damage, indicating early onset of the renal disease.

Figure 6H:
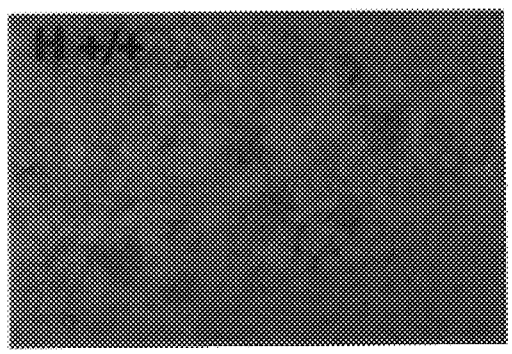
Figure 6I:
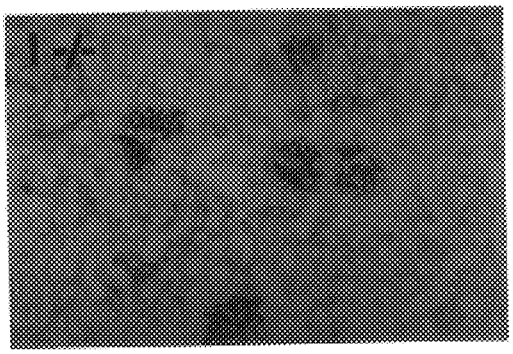
Figure 6J:
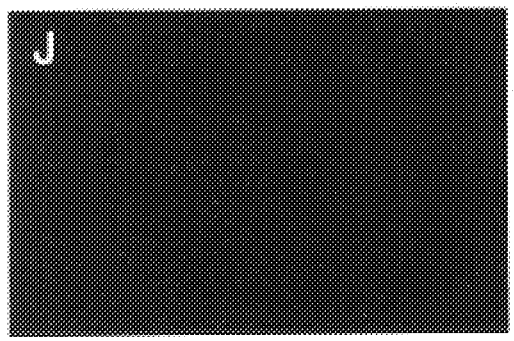

The possibility that the glomerulonephritic process was secondary to immune dysfunction was investigated. Immunochemical staining of frozen sections of kidney, using isotype-specific antibodies, showed deposition of IgG immune complexes in the glomeruli (FIG. 6I). This immune complex deposition was evident in mice at an early age. The presence of immune complexes was confirmed by electron microscopy, since subendothelial and mesangial electron dense deposits were identified.

Figure 6K:
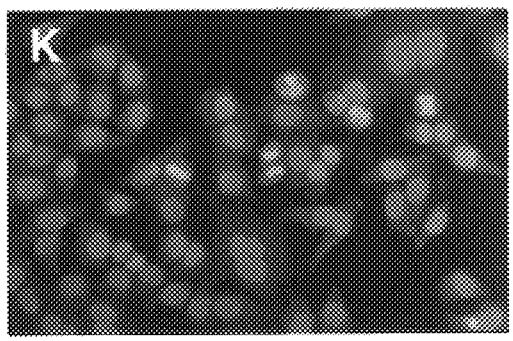
Figure 6L:
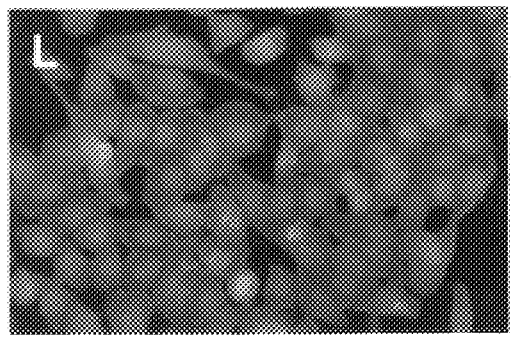
Figure 6M:
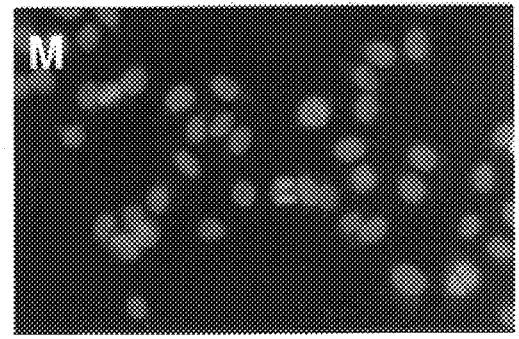

Immune complex glomerulonephritis is only seen when the precipitating antigen is persistent, as in chronic infections or autoimmune disease. The presence of autoreactive antibodies was therefore investigated by testing the capacity of sera from glomerulonephritic lyn –/– and control mice to react with autoantigens. While no staining was seen using serum from control mice (FIG. 6J), autoantibodies were evident in serum from glomerulonephritic lyn –/– mice (FIG. 6K–M). While most sera reacted with nuclear and cytoplasmic antigens (FIG. 6K, L), some reacted predominantly with nuclear antigens (FIG. 6M). Collectively these data indicate that the glomerulonephritis seen in lyn –/– mice is due to the deposition of IgG immune complexes containing autoreactive antibodies.

A survival study has shown that by 25 weeks of age, 42% of lyn –/– mice had either succumbed or were developing signs of autoimmune disease, as evidenced by the presence of blood in their urine. Moreover, over 90% of mice of more than 6 weeks of age showed histological signs of autoimmune disease.

EXAMPLE 8

Effect of Aging on Haematopoiesis in Lyn –/– Mice a) Depletion of Lymphoid Tissues With progressive aging, there is a significant depletion of lymphoid tissue in lyn –/– mice. In addition, extramedullary haematopoiesis is prominent in these mice, particularly in spleen and liver, but also in lymph node, lung, heart and kidney in some mice. In some instances the extramedullary haematopoiesis is correlated with bone marrow failure, and possibly also with chronic infection. Preliminary analysis of bone marrow and spleen progenitors in colony-forming cell assays suggests that these progenitors are elevated in aged lyn –/– mice.

The depletion of lymphoid tissue in aged lyn –/– mice is also correlated with an expansion of cells of myeloid origin that progress to malignant-like state. Such lesions have been found predominantly in spleen and lymph nodes, but have also been observed in liver and kidney. These lesions have the histological appearance of immature myelo/monocytic or histiocytic cells, and resemble histiocytic neoplasms.

b) Increased Colony-Forming Capacity of Haematopoietic Cells

Bone marrow and spleen cells from mice with such malignant-like lesions showed an increased capacity to form colonies in semi-solid agar cultures. In most cases the increase was 2–3 fold, but in some animals the increase was up to 50-fold. Such growth capacity renders the cells useful for the study of growth factors and of putative inhibitors of such factors.

Without wishing to be bound by any proposed mechanism for the observed effect, it is suggested that in the lyn –/– mice studied, there is either:

(a) a change in responsiveness of target cells to known growth factors;

(b) a change in concentration of a known growth factor, or (c) the action of a previously unknown haematopoietic growth factor, possibly produced by the "malignant" cells, may be responsible.

Alternatively such a factor may be produced by non-malignant cells, but exerts an effect which promotes development of malignancy.

The present invention thus provides a lyn –/– animal model, such as mice, which is useful for studying diseases associated with BCR-mediated signal transduction required for T-cell independent B cell proliferation. The reduction in the number of B cells in the lymphoid tissues of such animals makes the animals suitable for the study of B-cell development, diseases including autoimmune diseases, allergy, asthma and dysplasias of myeloid origin, and for the screening of therapeutic agents for the treatment or prevention of such diseases.

Double or multiple knock-out animals may also be produced by crossing a lyn –/– strain with one carrying the appropriate gene disruption(s), thus providing additional models for investigation of targeted gene deletion and/or related diseases.

The apparent failure of the lyn –/– mice to develop normal germinal centres also provides a convenient system for studying the T-dependent responses such as generation of high affinity antibodies or memory B cells, and the effects of antigen concentration on such responses.

B cell abnormalities associated with lyn –/– mice resemble those seen in the xid mouse, which is characterized by a mutation in btk (Thomas et al, 1993; Rawlings et al, 1993). The phenotypes, however, are not identical; B cell deficiency in xid mice is due to a maturational block, and xid mice show reduced levels of serum IgM. Despite these differences, the similarity between the lyn –/– and xid phenotypes is intriguing, and provides the ability to investigate whether btk and lyn may participate in the same signal transduction pathways.

The lyn –/– animals of the invention may also be compared with Oct-2 –/– mice, which have reduced numbers of B cells, fail to respond to TI mitogens, but proliferate and differentiate normally in response to T cell signals in vitro (Corcoran et al, 1993; Corcoran and Karvelas, 1994). However, normal levels of lyn message are present in Oct-2 –/– B cells (Corcoran and Karvelas, 1994).

Vav –/– mice also have diminished B cell responses to anti-Ig, although they respond normally to LPS (Tarakhovsky et al, 1995; Zhang et al, 1995), and may have reduced numbers of B cells (Tarakhovsky et al, 1995; Fischer et al, 1995). TD responses of vav –/– mice also appear to be normal (Tarakhovsky et al, 1995; Zhang et al, 1995).

The similarity of the B cell phenotypes of mice with mutations in different signal transduction molecules is consistent with the cascade of interactions believed to occur following ligation of the BCR (Pleiman et al, 1994b). The lyn –/– animals of the invention provide another model for studying BCR-related functions or more specifically, lyn deficiency.

The elevated levels of both IgM antibody and IgM secreting cells, and the existence of circulating autoantibodies in the lyn –/– mice are surprising, and provide additional basis for investigating B-cell depletion and autoimmunity in these mice. While examples of hyper IgM with an associated autoimmunity have been described in other strains of mice, the nature of these conditions appears to be distinct from that found in lyn –/– mice. In NZB mice and related strains, the hyper IgM and autoantibody production are associated with a B cell hyperplasia, particularly of the Ly-1 B cell subset (Hayakawa et al, 1983). Similarly, viable "motheaten" mice, which are affected by a severe autoimmune condition early in life, contain only Ly-1 B cells (Sidman et al, 1986). In contrast, the Ly-1 B cell subset is unchanged in lyn –/– mice (FIG. 2B).

The absence of normal germinal centres and the elevated levels of serum lgM found in lyn –/– mice are also seen in humans carrying a mutation in the gene encoding the CD40 ligand (Aruffo et al, 1993). Two observations indicate that the absence of normal germinal centres in lyn –/– mice is not due to a defect in CD40 signalling. Firstly, lyn −/− mice have normal IgG serum titres, and generate IgG1 antibodies in response to a TD antigen, whereas the CD40 ligand mutation results in agammaglobulinaemia (Aruffo et al, 1993). Secondly, lyn −/− B cells proliferate normally when stimulated through CD40.

As a result of the studies carried out using the present invention, it appears that the autoimmunity in lyn −/− mice is not a consequence of a change in the cellular composition of the B cell population, but rather results from altered signal transduction within each B cell. In this scheme, the differentiation of lyn −/− B cells into antibody-secreting cells results from aberrant processing of an Ig-mediated signal. It is possible that upon encountering self-antigens lyn −/− B cells are not deleted, nor unresponsive, but rather differentiate into plasma cells. While self-reactive IgM antibodies are usually considered relatively benign, they could assume pathological significance at high concentration. The immune complexes generated could act as a focal point for T-cell recruitment and the consequent development of a more pathological IgG-mediated condition. The glomerulonephritis and pancytopaenia seen in these mice bear many similarities to the renal and haematologic pathology manifested in systemic lupus erythematosus (SLE), a disease characterized by the production of multiple autoantibodies and immune complex deposition. In SLE, genetic susceptibility combined with an environmental trigger is thought to cause autoantibody production by B cells, at least in part because of abnormal B cell signalling (Mountz et al, 1991; Drake and Kotzin, 1992). The normal function of lyn may be critical for the maintenance of self-tolerance in the face of adverse environmental triggers, and the animals of the invention can be used to identify such triggers.

In addition to the importance of lyn in B cell signalling, the present results point to a critical role for lyn in mast cell function. The importance of FcεRI in the allergic response has previously been demonstrated in mice lacking this receptor because of disruption of either the α or γ subunit (Dombrowicz et al, 1993; Takai et al, 1994). We have shown that mice deficient in lyn are defective in mediating cutaneous anaphylaxis, and thus that lyn is directly implicated as a crucial signalling component of this receptor complex. This suggests that antagonists of lyn are useful to prevent or ameliorate IgE-mediated immune reactions, including allergy and asthma.

B cells can respond in a number of different ways to stimulation with antigen and their response is dependent on their state of differentiation and on the concentration of antigen. They can be induced to proliferate or to differentiate into antibody-producing cells or memory cells, and, under certain conditions, they can be either clonally deleted or made unresponsive. The data suggest that lyn is necessary not only for B cell proliferation, but also for clonal deletion of autoreactive B cells.

The present data indicate that the lyn −/− animal may be used as a model of malignant disease of cells of the myeloid lineage, such as those which are myelo/monocytic or histocytic in appearance, or for the study of factors involved in regulation of myelopoiesis.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Allen, D., Cumano, A., Dildrop, R., Kochs, C., Rajewsky, K., Rajewsky, N., Roes, J., Sablitzky, F. and Siekevitz, M. "Timing, genetic requirements and functional consequences of somatic hypermutation during B-cell development" Immunol. Rev., 1987 96 5–22.

Aruffo, A., Farrington, M., Hollenbaugh, D., Li, X., Milatovich, A., Nonoyama, S., Bajorath, J., Grosmaire, L. S., Stenkamp, R., Neubauer, M., Roberts, R. L., Noelle, R. J., Ledbetter, J. A., Francke, U. and Ochs, H. D. "The CD40 ligand, gp39, is defective in activated T cells from patients with X-linked hyper-IgM syndrome" Cell, 1993 72 291–300

Banchereau, J., Bazan, F., Blanchard, D., Briere, F., Galizzi, J. P., van Kooten, C., Liu, Y. J., Rousset, F. and Saeland, S. "The CD40 antigen and its ligand" Annu. Rev. Immunol., 1994 12 881–922.

Blank, U., Ra, C., Miller, L., White, K., Metzger, H. and Kinet, J-P. "Complete structure and expression in transfected cells of high affinity IgE receptor" Nature, 1989 337 187–189.

Bolen, J. B., Rowley, R. B., Spana, C. and Tsygankov, A. Y. "The src family of tyrosine protein kinases in hemopoietic signal transduction" FASEB J., 1992 6 3403–3409.

Burkhardt, A. L., Brunswick, M., Bolen, J. B. and Mond, J. J. "Anti-immunoglobulin stimulation of B lymphocytes activates src-related protein-tyrosine kinases" Proc. Natl. Acad. Sci. USA, 1991 88 7410–7414.

Campbell, M.-A. and Sefton, B. M. "Protein tyrosine phosphorylation is induced in murine B lymphocytes in response to stimulation with anti-immunoglobulin" EMBO, 1990 9 2125–2131.

Campbell, M-A. and Sefton, B. M. "Association between B-lymphocyte membrane immunoglobulin and multiple members of the src family of protein tyrosine kinases" Mol. Cell. Biol., 1992 12 2315–2321.

Clark, M. R., Campbell, K. S., Kazlauskas, A., Johnson, S. A., Hertz, M., Potter, T. A., Pleiman, C. and Cambier, J. C. "The B cell antigen receptor complex: association of Ig-a and Ig-b with distinct cytoplasmic effectors" Science, 1992 258 123–126.

Coffman, R. L., Lebman, D. A. and Rothman, P. "Mechanism and regulation of immunoglobulin isotype switching" Adv. Immunol., 1993 54 229–270.

Corcoran, L. M., Karvelas, M., Nossal, G. J. V., Ye, Z.-S., Jacks, T. and Baltimore, D. "Oct-2, although not required for early B-cell development, is critical for later B-cell maturation and for postnatal survival" Genes & Dev., 1993 7 570–582.

Corcoran, L. M. and Karvelas, M. "Oct-2 is required early in T cell-independent B cell activation for G, progression and for proliferation" Immunity, 1994 1 635–645.

Corey, S. J., Burkhardt, A. L., Bolen, J. B., Geahlen, R. L., Tkatch, L. S. and Tweardy, D. J. "Granulocyte colony-stimulating factor receptor signaling involves the formation of a three-component complex with Lyn and Syk protein-tyrosine kinases" Proc. Natl. Acad. Sci. USA, 1994 91 4683–4687.

Dombrowicz, D., Flamand, V., Brigman, K. K., Koller, B. H. and Kinet, J.-P. "Abolition of anaphylaxis by targeted disruption of the high affinity immunoglobulin E receptor a chain gene" Cell, 1993 75 969–976.

Drake, C. G. and Kotzin, B. L. "Genetic and immunological mechanisms in the pathogenesis of SLE" Curr. Opin. Immunol., 1992 4 733–740.

Eiseman, E. and Bolen, J. B. "Engagement of the high-affinity IgE receptor activates src protein-related tyrosine kinases" Nature, 1992 355 78–80.

Fischer, K.-D., Zmuidzinas, A., Gardner, S., Barbacid, M., Bernstein, A. and Guidos, C. "Defective T-cell receptor signalling and positive selection of Vav-deficient CD4+ CD8+ thymocytes" Nature, 1995 374 474–476.

Gold, M. R., Law, D., and DeFranco, A. L. "Stimulation of protein tyrosine phosphorylation by the B-lymphocyte antigen receptor" Nature, 1990 345 810–813.

Gold, M. R., Matsuuchi, L., Kelly, R. B., and DeFranco, A. L. "Tyrosine phosphorylation of components of the B-cell antigen receptors following receptor crosslinking" Proc. Natl. Acad. Sci. USA, 1991 88 3436–3440.

Handyside, A. H., O'Neil, G. T., Jones, M. and Hooper, M. L. "Use of BRL-conditioned media in combination with feeder layers to isolate a diploid embryonal stem cell line" Roux's Arch. Dev. Biol., 1989 198 8–55.

Hayakawa, K., Hardy, R. R., Parks, D. R. and Herzenberg, L. A. "The "Ly-1B" cell subpopulation in normal, immunodefective, and autoimmune mice" J. Exp. Med., 1983 157 202–218.

Hibbs, M. L., Stanley, E., Maglitto, R. and Dunn, A. R. "Identification of a duplication of the mouse Lyn gene" Gene, 1995 156 175–181.

Kishihara, K., Penninger, J., Wallace, V. A., Kundig, T. M., Kawai, K., Wakeham, A., Timms, E., Pfeffer, K., Ohashi, P. S., Thomas, M. L., Furlonger, C., Paige, C. J. and Mak, T. W. "Normal B lymphocyte development but impaired T cell maturation in CD45-exon 6 protein tyrosine phosphatase-deficient mice" Cell, 1993 74 143–156.

Lalor, P. A., Nossal, G. J. V., Sanderson, R. D., and McHeyzer-Williams, M. G. "Functional and molecular characterization of single, (4-hydroxy-3-nitrophenyl) acetyl (NP)-specific IgG1+ B cells from antibody-secreting and memory B cell pathways in the C57BL/6 immune response to NP" Eur. J. Immunol., 1992 22 3001–3011.

Mann, G. B., Fowler, K. J., Gabriel, A., Nice, E. C., Williams, R. L. and Dunn, A. R. "Mice with a null mutation of the TGFa gene have abnormal skin architecture, wavy hair, and curly whiskers and often develop corneal inflammation" Cell, 1993 73 249–261.

Moore, A. E., Sabachewsky, L., and Toolan, H. W. Cancer Reseach, 1955 15 598

Mountz, J. D., Gause, W. C., and Jonsson, R. "Murine models for systemic lupus erythematosus and Sjogren's syndrome" Curr. Opin. Rheumatol, 1991 3 738–756.

Pleiman, C. M., Abrams, C., Gauen, L. T., Bedzyk, W., Jongstra, J., Shaw, A. S., and Cambier, J. C. "Distinct $p53/p56^{lyn}$ and $P59^{fyn}$ domains associate with nonphosphorylated and phosphorylated Ig-a" Proc. Natl. Acad. Sci. USA, 1994a 91 4268–4272.

Pleiman, C. M., D'Ambrosio, D., and Cambier, J. C. "The B-cell antigen receptor complex: structure and signal transduction" Immunol. Today, 1994b 15 393–399.

Ravetch, J. V. "Fc receptors: rubor redux" Cell, 1994 78 553–560.

Rawlings, D. J., Saffran, D. C., Tsukada, S., Largaespada, D. A., Grimaldi, J. C., Cohen, L., Mohr, R. N., EBazan, J. F., Howard, M., Copeland, N. G., Jenkins, N. A. and Witte, O. N. "Mutation of unique region of Bruton's tyrosine kinase in immunodeficient XID mice" Science, 1993 261 358–361.

Ren, C. L., Morio, T., Fu, S. M. and Geha, R. S. "Signal transduction via CD40 involves activation of lyn kinase and phosphatidylinositol-3-kinase, and phosphorylation of phospholipase Cg2" J. Exp. Med., 1994 179 673–680.

Reth, M. "Antigen receptors on B lymphocytes" Ann. Rev. Cell Biol., 1992 10 97–121.

Sidman, C. L., Schultz, L. D., Hardy, R. R., Hayakawa, K. and Herzenberg, L. A. "Production of immunoglobulin isotypes by Ly-1+ B cells in viable motheaten and normal mice" Science, 1986 232 1423–1425.

Smith, K. G. C., Weiss, U., Rajewsky, K., Nossal, G. J. V. and Tarlinton, D. M. "Bcl-2 increases memory B cell recruitment but does not perturb selection in germinal centers" Immunity, 1994 1 803–813.

Stanley, E., Ralph, S., McEwen, S., Boulet, I., Holtzman, D. A., Lock, P. and Dunn, A. R. "Alternatively spliced murine lyn mRNAs encode distinct proteins" Mol. Cell. Biol., 1991 11 3399–3406.

Stefanova, I., Corcoran, M. L., Horak, E. M., Wahl, L. M., Bolen, J. B. and Horak, I. D. "Lipopolysaccharide induces activation of CD14-associated protein tyrosine kinase $p53/p56^{lyn}$" J. Biol. Chem., 1993 268 20725–20728.

Takai, T., Li, M., Sylvestre, D., Clynes, R. and Ravetch, J. V. "FcR g chain deletion results in pleiotrophic effector cell defects" Cell, 1994 76 519–529.

Tarakhovsky, A., Turner, M., Schaal, S., Mee, P. J., Duddy, L. P., Rajewsky, K. and Tybulewicz, V. L. J. "Defective antigen receptor-mediated proliferation of B and T cells in the absence of vav" Nature, 1995 374 467–470.

Thomas, J. D., Sideras, P., Smith, C. I. E., Vorechovsky, I., Chapman, V. and Paul, W. E. "Colocalization of X-linked agammaglobulinemia and X-linked immunodefiency genes" Science, 1993 261 355–358.

Tybulewicz, V. L. J., Crawford, C. E., Jackson, P. K., Bronson, R. T. and Mulligan, R. C. "Neonatal lethality and lymphopenia in mice with a homozygous disruption of the c-abl proto-oncogene" Cell, 1991 65 1153–1163.

Varmus, H. E. and Lowell, C. A. "Cancer genes and hematopoiesis" Blood, 1994 83 5–9.

Wechsler, R. J. and Monroe, J. G. "src-family tyrosine kinase p55fgr is expressed in murine splenic B cells and is activated in response to antigen receptor cross-linking" J. Immunol., 1995 154 3234–3244.

Wershil, B. K., Mekori, Y. A., Murakami, T. and Galli, S. J. "$^{125}$I-fibrin deposition in IgE-dependent immediate hypersensitivity reactions in mouse skin: demonstration of the role of mast cells using genetically mast cell-deficient mice locally reconstituted with cultured mast cells" J. Immunol., 1987 139 2605–2614.

Yamanashi, Y., Kakiuchi, T., Mizuguchi, J., Yamamoto, T. and Toyoshima, K. "Association of B cell antigen receptor with protein tyrosine kinase lyn" Science, 1991 251 192–194.

Zhang, R., Alt, F. W., Davidson, L., Orkin, S. H. and Swat, W. "Defective signalling through the T- and B-cell antigen receptors in lymphoid cell lacking the vav proto-oncogene" Nature, 1995 374 470–473.

Zhu, N., Liggitt, D., Debs, R. et al "Systemic gene expression after intravenous DNA delivery into adult mice" Science, 1993 261 209

We claim:

1. A transgenic mouse carrying a disruption in both alleles of a gene encoding a protein tyrosine kinase, lyn, such that expression of said tyrosine kinase is at a non-existent level, wherein the disruption causes said mouse to display a phenotype characterized by lyn deficiency which results in an autoimmune disease in said mouse, and at least one symptom selected from the group consisting of; depletion of lymphoid tissue with age progression, extramedullary hematopoiesis, expansion of myeloid cells, glomerulonephritis, and defective IgE-mediated anaphylactic response.

2. The transgenic mouse according to claim 1, wherein the disruption results in the inability of the non-human transgenic animal to produce enzymatically active lyn.

3. The transgenic mouse according to claim 1, wherein said gene encoding the protein tyrosine kinase lyn carries a mutation comprising deletion of the lyn promoter and the associated regulatory sequences of said gene that regulate expression of said lyn.

4. The transgenic mouse according to claim 3, wherein said deletion further comprises a deletion in intron 1 between a PstI site and an XbaI site, the PstI site being upstream of the lyn promoter, and the XbaI site being downstream of said lyn promoter.

5. The transgenic mouse according to claim 1, wherein the phenotype is displayed in said mouse by 6–8 weeks, of age.

6. A transgenic mouse carrying a disruption in both alleles of a gene encoding a protein tyrosine kinase, lyn, such that expression of said tyrosine kinase is at a non-existent level, wherein the disruption causes said mouse to display a phenotype characterized by lyn deficiency which results in impaired B cell function and/or pancytopaenia in said mouse.

7. The transgenic mouse of claim 1, wherein said autoimmune disease is selected from the group consisting of glomerulonephritis and pancytopaenia.

8. The transgenic mouse of claim 1, wherein said autoimmune disease manifests itself as lupus erythematosus.

9. A transgenic mouse carrying a disruption in both alleles of a gene encoding a protein tyrosine kinase, lyn, such that expression of the tyrosine kinase is at a non-existent level, wherein the disruption causes said mouse to display a phenotype characterized by lyn deficiency which results in a depletion of lymphoid tissue in said mouse.

10. A transgenic mouse carrying a disruption in both alleles of a gene encoding a protein tyrosine kinase, lyn, such that expression of the tyrosine kinase is at a non-existent level, wherein the disruption causes said mouse to display a phenotype characterized by lyn deficiency which results in a disease characterized by a malignancy of myeloid origin in said mouse.

11. The mouse of claim 10, wherein said malignancy is selected from the group consisting of myeloid leukemia, malignant histocytoma and histocytosis.

12. A transgenic mouse carrying a disruption in both alleles of a gene encoding a protein tyrosine kinase, lyn, such that expression of the tyrosine kinase is at a non-existent level, wherein the disruption causes said mouse to display a phenotype characterized by lyn deficiency, which results in defective IgE anaphylactic response in said mouse.

13. A cell-line derived from the transgenic mouse of claim 1.

14. A method of testing the efficacy of a treatment for an autoimmune disease associated with a non-existent level of protein tyrosine kinase, lyn, comprising subjecting the transgenic mouse of claim 1 to the putative treatment and determining the efficacy of said treatment.

15. The method according to claim 14, wherein said autoimmune disease is selected from the group consisting of allergy, asthma, a disease characterized by a malignancy of myeloid origin and a disease characterized by impaired B cell function.

16. The method according to claim 15, wherein said autoimmune disease is glomerulonephritis or pancytopenia.

17. The method according to claim 15, wherein said disease characterized by a malignancy of myeloid origin produces an overproduction of cells of the myeloid lineage.

18. The method according to claim 15, wherein said treatment comprises administering an analogue of lyn having tyrosine kinase activity to a subject in need thereof.

19. The method according to claim 14, wherein said autoimmune disease is lupus erythematosus.

20. The method according to claim 15, wherein said disease characterized by a malignancy is of myeloid origin and is selected from the group consisting of myeloid leukemia, malignant histocytoma and histocytosis.

21. A method for testing whether an agent is useful for treating a condition associated with non-existent level of lyn protein tyrosine kinase comprising administering said agent to the transgenic mouse of claim 1, and determining a level of lyn protein tyrosine kinase, wherein a change in said non-existent level towards a normal level is indicative of efficacy of said agent.

22. A method for determining whether an agent is useful for restoring B cell function comprising administering said agent to the transgenic mouse of claim 1, and determining any rise B cell function of said non-human transgenic mouse, wherein any rise B cell function is indicative of a restorative effect on B cell function of said agent.

\* \* \* \* \*

UNITED STATES PATENT AND TRADEMARK OFFICE
CERTIFICATE OF CORRECTION

PATENT NO. : 5,859,314
DATED : January 12, 1999
INVENTOR(S) : Hibbs et al.

It is certified that error appears in the above-identified patent and that said Letters Patent is hereby corrected as shown below:

Column 5,
Line 4, change "Kinas,e" to read as -- Kinase --.
Line 20, change "B200$^{lo}$" to read as -- B220$^{lo}$ --.
Line 24, change "mabs" to read as -- mAbs --.

Column 14,
Line 13, change "thromrbocytopaenia" to read as -- thrombocytopaenia --.

Column 18,
Line 50, change "G" to read as -- G$_1$ --.

Column 19,
Line 57, change "EBazan" to read as -- Bazan --.

Signed and Sealed this

Eighteenth Day of September, 2001

Attest:

NICHOLAS P. GODICI
Attesting Officer
Acting Director of the United States Patent and Trademark Office